(12) United States Patent
Barlow et al.

(10) Patent No.: US 6,183,515 B1
(45) Date of Patent: *Feb. 6, 2001

(54) ARTIFICIAL BONE IMPLANTS

(75) Inventors: Joel W. Barlow; Goonhee Lee; Richard H. Crawford; Joseph J. Beaman; Harris L. Marcus; Richard J. Lagow, all of Austin, TX (US)

(73) Assignee: Board of Regents, The University of Texas System, Austin, TX (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/832,882

(22) Filed: Apr. 4, 1997

Related U.S. Application Data

(63) Continuation of application No. 08/288,120, filed on Aug. 8, 1994, now Pat. No. 5,639,402.

(51) Int. Cl.⁷ ............................... A61F 2/28; B29C 35/08
(52) U.S. Cl. ................. 623/16.11; 264/497; 264/628; 264/632
(58) Field of Search ...................... 264/401, 497, 264/16, 19, 43, 628, 669, 670, 681, 632; 433/173; 623/16.11, 17.11, 19.12, 20.11, 23.11, 22.44, 18.11, 19.11

(56) References Cited

U.S. PATENT DOCUMENTS

| | | |
|---|---|---|
| 3,379,541 | 4/1968 | Tuvell . |
| 3,913,229 | 10/1975 | Driskell et al. . |
| 4,046,858 | 9/1977 | Barsa et al. . |
| 4,048,300 | 9/1977 | Tomlinson et al. . |
| 4,097,935 | 7/1978 | Jarcho . |
| 4,113,500 | 9/1978 | Ebihara et al. . |
| 4,131,597 | 12/1978 | Blüethgen et al. . |
| 4,135,935 | 1/1979 | Pfeil et al. . |
| 4,149,893 | 4/1979 | Aoki et al. . |
| 4,207,306 | 6/1980 | Jarcho . |
| 4,222,128 | 9/1980 | Tomonaga et al. . |
| 4,223,412 | 9/1980 | Aoyagi et al. . |
| 4,224,072 | 9/1980 | Stewart . |
| 4,230,455 | 10/1980 | Hidaka et al. . |
| 4,274,879 | 6/1981 | Irvine . |

(List continued on next page.)

FOREIGN PATENT DOCUMENTS

WO 92/08567    5/1992   (WO) .

OTHER PUBLICATIONS

European Search Report dated Dec. 16, 1999 for 95930121.9.
Albee, et al., "Studies in Bone Growth," Ann. Surg., 71:32–39, 1920.
Barlow, "Metallic and Ceramic Structures from Selective Laser Sintering of Composite Powders," 3rd International Conference on Rapid Prototyping, 73–79, 1992.
Bhaskar, et al., "Tissue reaction to intrabony ceramic implants," Oral Surg., 31:282–289, 1971.
Bovey, et al., "Emulsion Polymerization," Interscience Publishers, Inc., 352–356, 1955.
Cameron, et al., "Evaluation of a Biodegradable Ceramic," J. Biomed. Materials Res., 11:179–186, 1977.

(List continued on next page.)

*Primary Examiner*—Christopher A. Fiorilla
(74) *Attorney, Agent, or Firm*—Akin, Gump, Strauss Hauer & Feld, LLP

(57) ABSTRACT

A process for making bone implants from calcium phosphate powders is disclosed. This process involves selectively fusing layers of calcium powders that have been coated or mixed with polymer binders. The calcium powder mixture may be formed into layers and the polymer fused with a laser. Complex three-dimensional geometrical shapes can be automatically replicated or modified using this approach.

22 Claims, 11 Drawing Sheets

U.S. PATENT DOCUMENTS

| | | |
|---|---|---|
| 4,308,064 | 12/1981 | Takami et al. . |
| 4,324,772 | 4/1982 | Conn et al. . |
| 4,330,514 | 5/1982 | Nagai et al. . |
| 4,436,684 | 3/1984 | White . |
| 4,673,355 | 6/1987 | Farris et al. . |
| 4,693,986 | 9/1987 | Vit et al. . |
| 4,699,742 | 10/1987 | Nakamura et al. . |
| 4,737,411 | 4/1988 | Graves, Jr. et al. ................. 428/403 |
| 4,761,272 * | 8/1988 | Hucke ................................. 423/445 |
| 4,976,376 | 12/1990 | White et al. ........................... 623/16 |
| 5,076,869 | 12/1991 | Bourell et al. . |
| 5,132,143 | 7/1992 | Deckard . |
| 5,134,009 | 7/1992 | Ichitsuka et al. . |
| 5,152,791 | 10/1992 | Hakamatsuka et al. . |
| 5,182,170 | 1/1993 | Marcus et al. . |
| 5,284,695 | 2/1994 | Barlow et al. . |
| 5,370,692 | 12/1994 | Fink et al. ............................. 623/16 |
| 5,510,066 | 4/1996 | Fink et al. .......................... 264/40.1 |
| 5,616,294 | 4/1997 | Deckard . |
| 5,639,402 | 6/1997 | Barlow et al. . |
| B1 4,436,684 | 5/1988 | White . |

OTHER PUBLICATIONS

Capano, "The chemical synthesis and biomedical and dental applications of the first truly successful in vivo replacements for bones, teeth, and similar materials," Ph.D. Thesis, University of Texas at Austin, 1987. Title page to page XXV.

Corbridge, "Phosphorous: an Outline of its Chemistry, Biochemistry and Technology," Studies in Inorganic Chemistry 10, 224, 1990.

Cutright, et al., "Reaction of bone to tricalcium phosphate ceramic pellets," Oral Surg., 33:850–856, 1972.

De Groot, "Bioceramics consisting of calcium phosphate salts," Biomaterials, 1:47–50, 1980.

Ferraro, et al., "Analysis of $Ca_3(PO_4)_2$ Bone Implant in Ilium Canis to Assess Resorption", J. Dent. Res., 58–A:410, 1979.

German, "The Characteristics of Binders for Injection Molding," Powder Injection Molding, 99–103, 1990.

Hattori, et al., "Hydrothermal Preparation of Calcium Hydroxyapatite Powders," J. Am. Ceram. Soc., 73(6):1803–1805, 1990.

Hill, et al., "The Binary System $P_2O_5-2CaO.P_2O_5$, " Amer. J. Sci., 242:457–477, 542–562, 1944.

Holmes, "Bone Regeneration Within a Coralline Hydroxyapatite Implant," Plast. Rec. Surg., 63:626–633, 1979.

Hulbert et al., "History of Bioceramics," Ceramics in Surgery, 3–27, 1983.

Jarcho, et al., "Hydroxylapatite synthesis and characterization in dense polycrystalline form," J. Materials Science, 11:2027–2035, 1976.

Jarcho, et al., "Tissue, Cellular and Subcellular Events at a Bone–Ceramic Hydroxylapatite Interface," J. Bioeng., 1:79–92, 1977.

Köster, et al., "Experimenteller Knochenersatz durch resorbierbare Calciumphosphat–Keramik," Langenbecks Arch. Chir., 341:77–86, 1976.

Köster, et al., "Resorbierbare Calciumphosphatkeramik im Tierexperiment unter Belastung," Langenbecks Arch. Chir., 343:173–181, 1977.

Lee, et al., "Selective Laser Sintering of Bioceramic Materials for Implants," Solid Freeform Fabrication Proceedings, 376–380, Sep., 1993, and poster session, Aug. 9, 1993.

Lefebvre, "Atomization and Sprays," Purdue University, Hemisphere Publishing, 356–359, 1989.

Levy, et al., "Preliminary Experience with Selective Laser Sintering Models of the Human Temporal Bone," Am. J. Neuroradiology, 15:473–477, 1994.

Levy, et al., "Preliminary Experience with Selective Laser Sintigraphic (SLS) Models of the Human Temporal Bone," Solid Freeform Fabrication Symposium Proceedings, 3:161–173, 1992.

McIntosh, et al., "X–Ray Diffraction Powder Patterns of the Calcium Phosphates," Anal. Chem., 28(9):1424–1427, 1956.

Nelson, et al., "Evaluation of New High–Performance Calcium Polyphosphate Bioceramics as Bone Graft Materials," J. Oral & Maxillofac Surg., 51:1363–1371, 1993.

Nielson, "Filling of Sterile and Infected Bone Cavities by Means of Plaster of Paris," Acta Chir. Scandanav., 91:17–27, 1944.

Peltier, et al., "The Using of Plaster of Paris to Fill Defects in Bone," Ann. Surg., 146:61–69, 1957.

Vail, et al., "Development of a Poly(Methyl Methacrylate––co–n–Butyl Methacrylate) Copolymer Binder System," J. Appl. Polym. Sci., 52:789–812, 1994.

Vail, et al., "Silicon Carbide Preforms for Metal Infiltration by Selective Laser Sintering™ of Polymer Encapsulated Powders," Solid Freeform Fabrication Proceeding, 204–214, 1993.

Vail, et al., "Ceramic Structures by Selective Laser Sintering of Microencapsulated, Finely Divided Ceramic Materials," Solid Freeform Fabrication Symposium Proceedings, 3:124–130, 1992.

Vail, et al., "Effect of Polymer Coatings as Intermediate Binders on Sintering of Ceramic Parts," Solid Freeform Fabrication Symposium Proceedings, 2:195–205, 1991.

Van Wazer, "Phosphorous and Its Compounds," Interscience Publisher, 1:517–522, 1958.

Yoshihiro, "Studies of Calcium Phosphate Glass–Ceramics," Shika Rikogaku Zasshi, 16:196–202, 1975. (Abstract only).

Lee, et al., "Selective Laser Sintering of Calcium Phosphate Powders," Solid Freeform Fabrication Symposium Proceedings, Sep. 1–7, 1994.

Hogan, "The Perfect Prosthesis," Natural Science—At The Edge, Jan. 1990.

Dialog Search, Jul. 29, 1994.

Lee et al., "Biocompatibility of SLS–Formed Calcium Phosphate Implants," Solid Freeform Fabrication Proceedings, pp. 15–21, Sep. 1996, Symposium in Austin, Texas, Aug. 12–14, 1996.

* cited by examiner

ARTIFICIAL BONE IMPLANTS

This application is a continuation application of co-pending U.S. Ser. No. 08/288,120, filed Aug. 8, 1994 now U.S. Pat. No. 5,639,402.

The U.S. government owns rights in the present invention as relevant developmental work was supported by DARPA/ONR (Grant No. N000014-92-J-1394).

BACKGROUND OF THE INVENTION

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

A bibliography of references cited herein is included at the id end of this specification. The references listed in the bibliography, to the extent that they provide exemplary procedural or other details supplementary to those set forth herein, are specifically incorporated herein by reference.

1. Field of the Invention

The present invention relates generally to manufacturing methods and systems (collectively referred to as "processes") for the freeform shaping of calcium-containing powders. This invention more specifically relates to processes for shaping bone implants from various calcium phosphate powders and polymer-emulsion binders. Certain embodiments of these processes focus on the use of a Selective Laser Sintering™ ("SLS™") device to automatically and selectively fuse the polymer binder. In such processes, complex three-dimensional objects may be built by selectively fusing successive thin layers of the powdered material.

2. Description of the Related Art

Much attention has been given in the art to the development of materials to assist in the regeneration of bone defects and injuries. In 1926, DeJong observed the similarities between the powder X-ray diffraction pattern of the in vivo mineral and the hydroxyapatite $(Ca_5(OH) (PO_4)_3$, "CHA"). Calcium compounds, including calcium sulfate (Nielson, 1944), calcium hydroxide (Peltier, 1957), and tricalcium phosphate ("TCP") (Albee et al., 1920), have been observed to stimulate new bone growth when implanted or injected into bone cavities (Hulbert et al., 1983). These materials also exhibit good biocompatibility and compositional similarities to human bone and tooth and can serve as resorbable or non-resorbable implants depending on their degree of microporosity.

Some TCP implants are known to be readily resorbable. For example, sintered TCP plugs with pore sizes between 100–200 microns have been implanted in rats (Bhashar et al., 1971). Very rapid bone formation was reportedly observed at three days after implantation, and highly cellular tissue, consisting of osteoblastic and fibroblastic proliferation, was found within the pores. At one week, the size of the implant was reduced, and new bone formation was extensive. After two weeks, connective tissue had infiltrated throughout the ceramic. During the next four weeks, the boney material within the ceramic continued to mature. Electron micrographs indicated that within clastlike cells, ceramic could be depicted in membrane-bound vesicles. The authors concluded that TCP implants were biodegradable, via phagocytosis, the ceramic did not elicit a marked inflammatory response, and connective tissue grew rapidly within the pores.

Similar results have also been reported by Cutright et al. (1972) who also implanted TCP in rat tibiae. In this study, the ceramic cavities were filled with osteoid and bone after 21 days and the TCP implant was no longer detectable after 48 days.

Larger implants in dogs are reported to elicit slower responses. Cameron et al. (1977) found that TCP implants in dog femurs were completely infiltrated with new bone by four weeks. However, after six weeks, the rate of new bone growth had slowed as the TCP was resorbed. Additionally, only 15% of a 2 cm×2 cm iliac TCP implant in dogs was resorbed after 18 monthsa (Ferraro et al., 1979).

Koster et al. (1976) reported the testing of the calcium phosphate formulations monocalcium phosphate, dicalcium phosphate, tricalcium phosphate, tetracalcium phosphate, and combinations consisting of 20% monocalcium phosphate and 80% of either di-, tri- or tetracalcium phosphate as implant materials in dog tibiae. These investigators tested both dense ceramics and porous ceramics with pore sizes between 800–1000 microns. They reported that tissue compatibility is dependent on the $CaO/P_2O_5$ ratio. All materials with ratios between 2/1 and 4/1 are compatible with the optimum ratio being about 3/1 for TCP. After 10 months, Koster et al. (1977) found that tetracalcium phosphate was resorbed only to a minor extent, but that TCP demonstrated lamellar bone growth throughout its pores. Both were found to be tissue compatible. The authors stated that the 3/1 material was not as strong as the 4/1 material and suggested that TCP should be used only in low stress areas while tetracalcium phosphate could be used in high stress environments.

Jarcho et al. (1976, 1977) reported the development of a process for preparing dense, polycrystalline, calcium hydroxyapatite (CHA), with the empirical formula $2(Ca_5 (PO_4)_3OH)$ or $(3Ca_3 (PO_4)_2) Ca(OH)_2$. In this study, plugs were fabricated at 100% density and implanted in dogs. No evidence of tissue inflammation occurred, and in contrast to the porous TCP implants described above, little resorption or biodegradation was observed after six months.

Holmes (1979) reported that resorption did occur in porous CHA structures. These results led deGroot (1980) to suggest that all calcium phosphates are degradable (resorbable), but the rate is determined by the degree of microporosity. A dense calcium phosphate with negligible porosity would thus degrade only nominally. These results seem to be verified by Farris et al. (U.S. Pat. No. 4,673,355), who claim biocompatible materials with good properties over the range of Ca/P atomic, or molar, ratios from 0.1 to 1.34. (All patents and patent applications cited herein are incorporated by reference.) These ratios convert to $CaO/P_2O_5$ ratios between 0.2 and 2.68, lower than the 3.0 ratio suggested above. They suggest that the Ca/P or $CaO/P_2O_5$ ratio is not critical for implant applications. Ca/P ratios in the range 0.1 to 2.0 probably show satisfactory biocompatibility. Capano (1987) found that a Ca/P ratio of 0.5, which corresponds to calcium metaphosphate ("CMP"), has the best biocompatibility when implanted in small animals.

As the apatites are nearly identical in properties and chemical compositions to bone and tooth enamel, a considerable amount of synthetic effort has been done in this area. Patents in this area include: U.S. Pat. No. 4,046,858; U.S. Pat. No. 4,274,879; U.S. Pat. No. 4,330,514; U.S. Pat. No. 4,324,772; U.S. Pat. No. 4,048,300; U.S. Pat. No. 4,097,935; U.S. Pat. No. 4,207,306; and U.S. Pat. No. 3,379,541.

Several patents describe methods for treating apatite materials to render implantable shapes. These methods of heating and compaction under pressure in molds produce solid porous articles in various shapes. These patents include: U.S. Pat. No. 4,673,355; U.S. Pat. No. 4,308,064; U.S. Pat. No. 4,113,500; U.S. Pat. No. 4,222,128; U.S. Pat. No. 4,135,935; U.S. Pat. No. 4,149,893; and U.S. Pat. No. 3,913,229.

Several patents speak to the use of laser radiation to bond apatite materials to tooth and other surfaces, for example, U.S. Pat. No. 4,673,355 and U.S. Pat. No. 4,224,072.

Other patents describe the use of particulate or compacted apatite in conjunction with various compounds, filler, and cements, for example, U.S. Pat. No. 4,673,355; U.S. Pat. No. 4,230,455; U.S. Pat. No. 4,223,412; and U.S. Pat. No. 4,131,597.

The above discussion indicates that calcium phosphates or compounds, such as CHA that are substantially TCP (Monsanto, for example, markets CHA as TCP), are useful for a variety of bioceramic applications because they are biocompatible and can be fabricated into shapes that have a desirable combination of strength, porosity, and longevity for particular sorbable and non-sorbable needs.

Virtually any calcium and phosphate source can be used to prepare materials of interest. An important issue is the ratio of Ca to P or, as it is usually expressed, CaO to $P_2O_5$ molar ratio in the reactant mixture. For example, one can prepare monocalcium orthophosphate monohydrate from the reaction of CaO with orthophosphoric acid, $H_3PO_4$, as shown in equation 1:

$$CaO + H_3PO_4 \xrightarrow{<100°\,C.} Ca(H_2PO_4)_2 \cdot H_2O \qquad (1)$$

One could also react CHA with $H_3PO_4$ to achieve the same product, as shown in equation 2:

$$2(Ca_5(PO_4)_3OH) + 14H_3PO_4 \xrightarrow{<100°\,C.} 10Ca(H_2PO_4)_2 \cdot H_2O \qquad (4)$$

Heating the orthophosphate hydrate can lead to a variety of known products, depending on the firing temperature used, as shown in equations 3–8:

$$Ca(H_2PO_4)_2 \cdot H_2O \xrightarrow{100-130°\,C.} Ca(H_2PO_4)_2 + H_2O \qquad (3)$$

$$Ca(H_2PO_4)_2 \cdot H_2O \xrightarrow{170°\,C.} CaH_2P_2O_7 + 2H_2O \qquad (4)$$

$$Ca(H_2PO_4)_2 \cdot H_2O \xrightarrow{250°\,C.} Ca(PO_3)_2(a) + 3H_2O \qquad (5)$$

$$Ca(PO_3)_2(a) \xrightarrow{450°\,C.} \delta - Ca(PO_3)_2 \qquad (6)$$

$$Ca(PO_3)_2(a) \xrightarrow{500°\,C.} \beta - Ca(PO_3)_2 \qquad (7)$$

$$\beta - Ca(PO_3)_2 \xrightarrow{970°\,C.} \alpha - Ca(PO_3)_2 \qquad (8)$$

The α-, β-, and δ-forms of calcium metaphosphate are different crystal structures of the same chemical compound that happen to be stable at different temperatures. Tricalcium phosphates can be easily obtained from CHA by simply lowering the Ca/P ratio, as shown in equation 9:

$$3[2(Ca_5(PO_4)_3OH)] + 2H_3PO_4 \xrightarrow{<100°\,C.} 10Ca_3(PO_4)_2 \cdot 6H_2O \qquad (9)$$

According to McIntosh et al. (1956), the orthophosphate hydrate can be converted to two crystalline forms by heating, as shown in equations 10–11:

$$Ca_3(PO_4)_2 \cdot 6H_2O \xrightarrow{680°\,C.} \beta - Ca_3(PO_4)_2 + H_2O \qquad (10)$$

$$\beta - Ca_3(PO_4)_2 \xrightarrow{1150°\,C.} \alpha - Ca_3(PO_4)_2 \qquad (11)$$

Similar reaction schemes can be written for producing di-calcium and tetra-calcium phosphates from CHA or any other calcium source by reacting with orthophosphoric acid or any other $P_2O_5$ source. The chemical and crystalline forms of the final product are simply set by the Ca/P or $CaO/P_2O_5$ molar ratio and the final temperature.

Five calcium phosphates which exhibit different x-ray diffraction patterns are known to be precipitated from aqueous solution at normal pressure (Van Wazer, 1958). These are $Ca(H_2PO_4)_2$, $Ca(H_2PO_4)_2 \cdot H_2$ $CaHPO_4$, $CaHPO_4 \cdot 2H_2O$, and crystalline precipitate of variable composition of hydroxyapatite with the base formula $Ca_5(OH)(PO_4)_3$. Various forms of calcium phosphate compounds, Ca/P ratio range from 0.5 to 1, are prepared from the reaction of calcium hydroxyapatite with phosphoric acid.

Thermally dehydrated calcium phosphates are known to form a CaO and $P_2O_5$ binary system. For the CaO and $P_2O_5$ binary system, the chain phosphates appear between the orthophosphate (mole ratio of $CaO/P_2O_5$ of about 3) and metaphosphate (mole ratio of $CaO/P_2O_5$ of about 1) or ultraphosphate (mole ratio of $CaO/P_2O_5$ of less than 1). The metaphosphates, in particular, generally exhibit very high degrees of polymerization and good mechanical properties. In this binary system, with a mole ratio of $CaO/P_2O_5$ less than 55/45, a glass-like structure forms from the melt which has mechanical properties similar to those of natural teeth (Yoshihiro, 1975).

Many studies and methods, from powder compaction sintering to hot isostatic pressing, have been reported for the fabrication of CHA implants. However, sintered CHA materials by conventional techniques are generally as weak as sea coral even at high compacting pressure, because CHA decomposes at temperatures lower than the required temperature for sintering.

Some more recent advances are the development of hydroxyapatite (CHA) and calcium phosphate powders that can be processed to yield porous resorbable bone facsimiles (U.S. Pat. No. 4,673,355); the development of the SLS™ process for directly shaping complex porous structures from thermally fusible polymer/ceramic powders without molds (U.S. Pat. No. 5,076,869); the development of low temperature infiltration and cementing techniques to prepare and replace the polymer binder with ceramic binder (U.S. Pat. No. 5,284,695); and the development of techniques for converting computed tomographic ("CT") information into three-dimensional mathematical files that can automatically guide the SLS™ process (Levy et al., 1992; Levy et al., 1994).

More recent work has been directed at expanding the utility of the SLS™ apparatus by preparing polymer-coated ceramic powders from spray dried mixtures of water, inorganic particulate, and a custom-synthesized, emulsified, nanometer-sized, polymer binder (Barlow, 1992; Vail et al., 1992). Ceramic composites made by this approach are relatively large, 10–50 microns, agglomerates of polymer-coated inorganic particles. These agglomerate powders may spread easily into uniform layers and fuse readily in the SLS™ machine to yield porous "green" parts that have relative densities near 50%, excellent connected internal porosity, and sufficient strengths to be easily handled and shipped. Interconnected pores in bioceramics are often difficult to achieve and are very important in fostering borne growth and for preparing metal matrix/ceramic parts, e.g., artificial hips.

Polymethyl methacrylate (PMMA) has also been used to form green composites with alumina and with silica/zircon (U.S. Pat. No. 5,284,695). In this process, an appropriate ceramic silicate colloid is used to infiltrate the connected pores of the polymer-bound green part, the colloid is solidified below the fusion temperature of the binder to maintain part geometry, the binder is then thermally removed and the part fired at typically 1000° C. to form porous, all ceramic parts that are suitable for use as cores and molds for metal castings. Such parts typically have only a 1% linear shrinkage, relative to the green state. Their strengths and porosities can be adjusted by additional infiltration and firing treatments.

Lagow and co-workers have recently described the chemical synthesis of high strength CHA (U.S. Pat. No. 4,673,355) and long-chain calcium polyphosphate bioceramic powders ("CPB") (Capano, 1987; Nelson et al., 1993). CPB powder is a pure calcium phosphate material with condensed phosphate chains (as shown below) with degrees of polymerization often greater than 120.

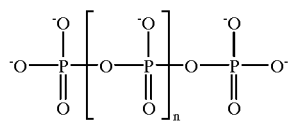

These materials produce sintered materials that have compressive strengths greater than 200,000 psi and flexural strengths in excess of 20,000 psi. These strengths are about twice that of porcelain used to make dental crowns. Using the Lagow CHA material, Lagow and Friedman have recently completed the first successful, year duration, mandible implant in a canine. Work with CPB implants has demonstrated by electron microscopy backscattering that new bone growth occupied nearly 55% of the volume of a CPB implant in the alveolar (tooth bearing) ridge of a dog, after only four months (Nelson et al., 1993). This rate of resorption and replacement by living bone in CPB is about twice as fast as that in CHA.

The lack of suitable bone replacement is a general problem that can be potentially solved by the development of synthetic bones and bone templates that are converted to bone by the body. Bone banks currently provide gamma radiation-treated cadaver bones for various orthopedic and reconstructive purposes in a world-wide business. Appropriate geometries are not always available from these sources, and there is some concern about the transmission of HIV and other diseases. For example, in connection with spinal fusions, there is a substantial need for wedge materials that can provide support and promote the deposition of additional bone. These needs could be rapidly multiplied, provided viable materials and processes could be developed to readily provide bone materials that are shaped to the needs of each individual patient.

Facial and cranial reconstructive surgery is an area where the need for individual implant geometries is especially critical. At present, such reconstructions tend to be very difficult surgical procedures, typically involving highly skilled grafting with allogenic bone. The method and system of the present invention can be utilized to accurately construct a complete facsimile bone structure, suitable for implantation, employing geometric information that is obtained from either CT data or a Computer Aided Design ("CAD") software package.

SUMMARY OF THE INVENTION

The present invention addresses the foregoing and other problems experienced in the art by providing processes for automatically shaping bone implants from various calcium phosphate powders. This invention employs polymeric binder compositions particularly adapted for the formulation of free flowing calcium phosphate/binder composite powders. The powders are suitable for production of bioceramic computer-modeled geometrical implants. Green parts produced in this manner may be post processed to be substantially free of the binder. This invention also allows bioceramic parts to be produced by the low power lasers used in the laser sintering process. The processes may utilize a process called Selective Laser Sintering™ in which complex three-dimensional objects can be built automatically by selectively fusing successive thin layers of powdered material.

One embodiment of the present invention provides a method for making an implant by forming a mixture of a calcium phosphate and a polymer binder, and selectively fusing the polymer binder to form an implant. These steps can be repeated to prepare a multiple-layered implant by successively forming layers of the calcium phosphate and polymer binder mixture, and selectively fusing the polymer binder in that layer and to other adjacent layers to form a plurality of connected layers.

As used herein the term "implant" refers to a device that is fabricated for the purpose of embedding, or placing, within a body. The types of implants encompassed by the present invention include implants suitable for the replacement, repair, or modification of bones, teeth, and the like. However, under certain circumstances it may be conceivable that implants of the present invention may serve other useful purposes.

As used herein the term "selectively fusing" refers to the process of selectively coalescing, or combining, particles such that the formed structure has sufficient strength to be handled and further processed, as desired. The term "selectively" is used to denote the controlled and discriminating fashion with which the fusing process occurs. In this aspect of the present invention, "fusing" refers to the viscous sintering of polymer binder particles that are coating, or otherwise associating with, calcium phosphate particles. This results in a linking of the calcium phosphate particles into a part, which can be further processed by thermally decomposing and removing the polymer binder or by infiltration and subsequent thermal dehydration and the like. This fusing can generally be accomplished selectively by controlling the spatial arrangement of the interconnected particles, for example, with laser sintering processes and the like. Alternatively, the selective fusing could be accomplished using a thermal mask system or by the selective spraying of liquid binders and solvents.

The thickness of the layers formed in this method is preferably from about 3 to about 12 thousandths of an inch. In cases where CT data is employed to shape the implant, the thickness of the layers may be determined by the CT data.

The calcium phosphate is preferably prepared by reacting a mixture of hydroxyapatite and phosphoric acid, although other calcium phosphates can be used. Preferred calcium phosphates include calcium metaphosphate, calcium pyrophosphate, calcium phosphate with from about 25 to about 45 percent by weight calcium oxide, and calcium phosphate with from about 0.5 to about 2 percent by weight sodium oxide, with calcium metaphosphate being particularly preferred.

The calcium phosphate preferably has a mean particle size of from about 5 to 100 microns, with the range of from about 30 to 50 microns being most preferred. Smaller particles tend to produce weaker green parts whereas larger particles can affect the layer thickness and forming.

Certain embodiments of this invention involve coating the calcium phosphate particles with polymeric binders to provide free-flowing powders with advantageous properties for processing into shapes by sintering with a laser beam. The polymeric binder compositions may be employed to mix with, or to coat, ceramic particles to produce free-flowing powders with flow characteristics substantially independent of relative humidity.

The polymer binder may be selectively fused to replicate or form a desired geometrical shape, such as a bone or an enhancement of a bone feature. This desired geometrical shape may be obtained from CT data or CAD software data and communicated to a laser beam by a computer.

The calcium phosphate powder may be mixed with water and a polymer-emulsion binder to form a slurry. In a preferred embodiment, this slurry is rapidly dried by momentarily suspending drops of it in a stream of hot air at a temperature above the fusion temperature of the binder, such as exists in a spray drier or fluidized bed coater. The binder and powder preferably agglomerate and adhere together to form a free flowing composite powder with preferred dimensions in the range of 5–75 $\mu$m.

Although it is preferable that the mixture be in the form of agglomerated polymer-coated calcium phosphate particles, mixtures or uncoated calcium phosphate powder and spray dried polymer binder can also be used. Coating the calcium phosphate with the binder is preferred as the polymer binder is used more efficiently in this embodiment, and the coating reduces segregation by density during storing or transporting.

As used herein the term "agglomerated polymer-coated calcium phosphate particles" refers to an indiscriminately formed cluster of particles consisting of calcium phosphate powders that have been coated with a polymer binder. These clusters may be free-flowing substantially independent of the relative humidity.

The implant may be thermally sintered. This can effectively remove the polymer binder, and sinter, or fuse, the calcium phosphate powder.

As used in this aspect of the invention, the terms "sinter" and "sintering" refer to the forming of a coherent bonded mass by heating without melting. In the case of post-processing, the calcium phosphate particles may be combined into a coherent mass with heating, whereas in sintering by laser the polymer binders may be selectively fused by the low energy of the laser beam employed.

Alternatively or in addition to thermal sintering, the implant may be infiltrated with a calcium phosphate solution or the like. This may decrease shrinkage in the implant and also modify the relative density, porosity, and other properties of the implant.

As used herein the term "infiltrating" refers to a process in which a porous implant is placed in an aqueous solution of an inorganic material. This allows the solution to fill the interconnected pores of the implant, and thus upon drying deposit the inorganic material inside the implant. A further thermal sintering step may be undertaken to fuse or coalesce the calcium phosphate.

Preferred polymeric binders include those formed from 1,1-disubstituted vinyl monomers such as esters and amides of methacrylic acid and its derivatives. Examples of 1,1-disubstituted vinyl monomers include methacrylic acid, dimethylamino ethylmethacrylate and methacrylamide, methyl methacrylate and butyl methacrylate. The polymers formed from these monomers are particularly preferred because the major thermal decomposition route is depolymerization to gaseous products in both oxidizing and reducing atmospheres, largely eliminating problems with residual ash.

As used herein the phrase "homopolymer, copolymer, or terpolymer of methyl methacrylate" refers to polymers that are formed by polymerizing methyl methacrylate. These polymers may be formed by the homopolymerization of methyl methacrylate or by polymerizing methyl methacrylate with one or more other monomers.

Another embodiment of the present invention encompasses the implants produced by the previously described methods. These implants preferably have a mean pore size of from about 50 to about 300 microns and a percent relative density of from about 50 to about 806. As used herein the term "percent relative density" refers to the ratio of the implant density to the calcium phosphate density multiplied by one hundred. As defined, the percent relative density can be used to obtain the percent porosity by subtracting the percent relative density from one hundred.

Another embodiment of the present invention provides a system for making an implant, comprising a mixture of a calcium phosphate and a polymer binder, and means for selectively fusing the polymer binder to form an implant. The fusing means may comprise a laser sintering machine. The system may additionally comprise means for controlling the fusing means in order to form an implant having a desired geometrical shape. This controlling means may be a computer that obtains information about the desired geometrical shape from patient computed tomographic data or Computer Aided Design software.

DETAILED DESCRIPTION OF PREFERRED EMBODIMENTS

Figure 2:
FIG. 2 is a scanning electron micrograph of calcium hydroxyapatite at 1000 times magnification.

Certain embodiments of the present invention provide processes capable of fabricating complex three-dimensional implants made of calcium phosphates. A preferred source of calcium phosphate is from the reaction of hydroxyapatite and orthophosphoric acid. CHA powders are generally very cohesive and consist of very porous agglomerates with mean particle size of 1 to 2 $\mu$m and bulk density of less than 0.4 g/cm$^3$ (Hattori et al., 1990). The surface area of such powders determined by Mercury intrusion analysis is about 60 m$^2$/g, suggesting very small particles. Stoichiometric CHA contains constitutional water in the form of OH$^-$ ions. This water can be driven off at 1200° C. In addition, CHA is somewhat hygroscopic and will adsorb water from the atmosphere. This physically bound water forms steam when the powder is heated above 100° C. This interferes with the SLS™ process. FIG. 2 shows the microstructure of finely divided CHA powders.

Figure 7:
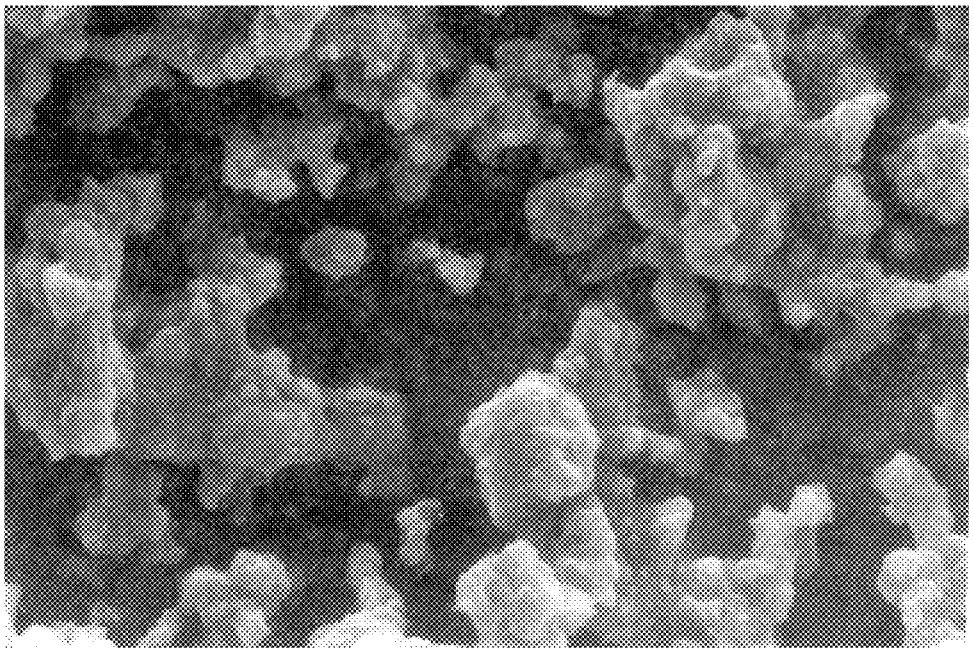
FIG. 7 is a scanning electron micrograph of calcium hydroxyapatite which has been reacted with orthophosphoric acid, shown at 1000 times magnification.
Figure 8:
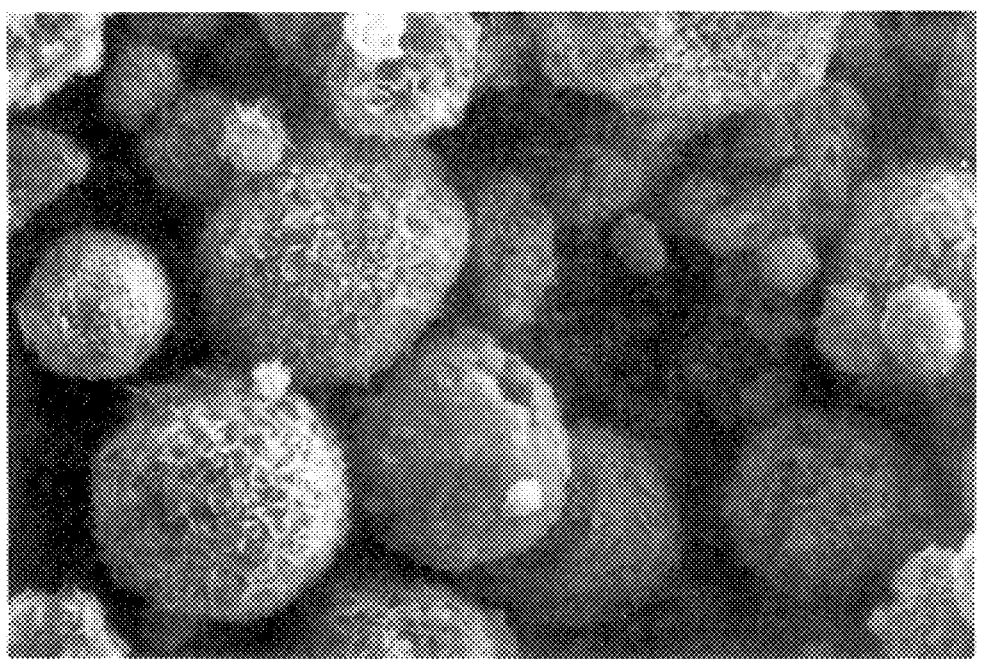
FIG. 8 is a scanning electron micrograph of a polymer coated powder, shown at 800 times magnification.

These powders generally require high sintering temperatures, and therefore typically are not suitable substrates for SLS™ processing. However, coating these powders with polymer binders that can fuse under much milder conditions may alleviate this problem. Such coated particles are shown in FIG. 8 as compared to non-coated particles of CHA which are shown in FIG. 7. As used in this invention, these coated particles may provide excellent substrates for producing bioceramic implants in laser sintering processes. The binder coated calcium phosphate powders may be readily handled, conveniently shipped and may be stored for long periods of time without the separation of components sometimes encountered when using mixed powders. In addition, one may readily produce green parts that can be post-processed to be free of polymer binder.

It is preferred that the polymer be distributed so as to cover as much of the surface of the particulate as possible. In principle, this could be accomplished by dissolving the polymer in a suitable organic solvent to achieve a low concentration of the polymer, depositing the solution on the surface of the particulate, then evaporating the solvent. However, this process has the disadvantage of solvent recovery costs as well as potential environmental harm associated with use of organic solvents. To address this problem, the amorphous polymeric binders preferably are prepared by emulsion polymerization as described in the literature (U.S. patent application Ser. No. 08/279,235 filed on Jul. 22, 1994, which is commonly owned with this application; Vail et al., 1994).

Many polymers can be made by emulsion polymerization. In this technique, liquid monomers are emulsified in water with the aid of an appropriate emulsifying agent. Waterborne, ionic initiators are incorporated to polymerize the monomer, thereby forming the desired emulsified polymer. Emulsion particles are typically quite small, about 100 nm (4×10$^6$ in) in diameter, so that the polymer is well distributed throughout the water vehicle with concentrations in the range of 2–5×10$^{14}$ particles per cubic centimeter (Bovey et al., 1955). In general, such emulsions are mechanically stable to the effects of gravity. Emulsion polymerization is generally known to produce high molecular weight products at high polymerization rates and is the method of choice for preparing the polymer binder commonly used in water-based acrylic paint systems.

To be effective in green part production and subsequent binder removal, the polymer binder should soften and flow at temperatures between 40° C. and 100° C. Additionally, the polymer coating should be rigid and non-tacky at room temperature. This reduces "blocking" or premature fusing of the polymer-coated powder during storage and provides some structural permanence (low creep rates and low flexibility at ambient temperature) to composite parts made from this powder.

The polymer's fusion temperature is a function of its molecular constituents. This temperature is characterized by the polymer's glass transition temperature, $T_g$, if the polymer is amorphous, or by its melting temperature, $T_m$, if it is semi-crystalline. The compositions employed in the present invention may be prepared from water based emulsions. This places a limit on the number of molecular constituents that are useful to give an amorphous polymer with a $T_g$ in the desired range. An upper limit of 100° C. for the softening temperature is set by the normal boiling point of the water vehicle in the emulsion. Regardless of the process used for coating the calcium phosphate particles with polymer binder, the surface temperature of the particle will be limited to 100° C. as long as a water film is present. The lower limit of the softening temperature may be set to about 40° C. to prevent blocking and creeping at ambient temperatures.

To prevent "fines" that can cause powder spreading problems in the laser sintering processes, it is desirable for polymer flow, film formation, and wetting of the inorganic surface to occur simultaneously with water evaporation. This generally cannot occur if the binder softening temperature greatly exceeds the normal boiling point of water.

Regardless of the polymer or copolymer composition used for the binder, the green strength and agglomerate morphology are related to the binder's ability to rapidly wet the inorganic particle during the coating process. These polymeric binders can be synthesized in emulsion form at controlled viscosity (Vail et al., 1994). The viscosity and the related melt flow index are held in the desired range by the addition of chain transfer agents to the polymerization reactions. The lower viscosity material will have an increased melt flow index, near 30 g/10 min at 200° C. and 75 psi, to optimize the coating characteristics of the polymer binder and the subsequent strength of the green part.

Figure 1:
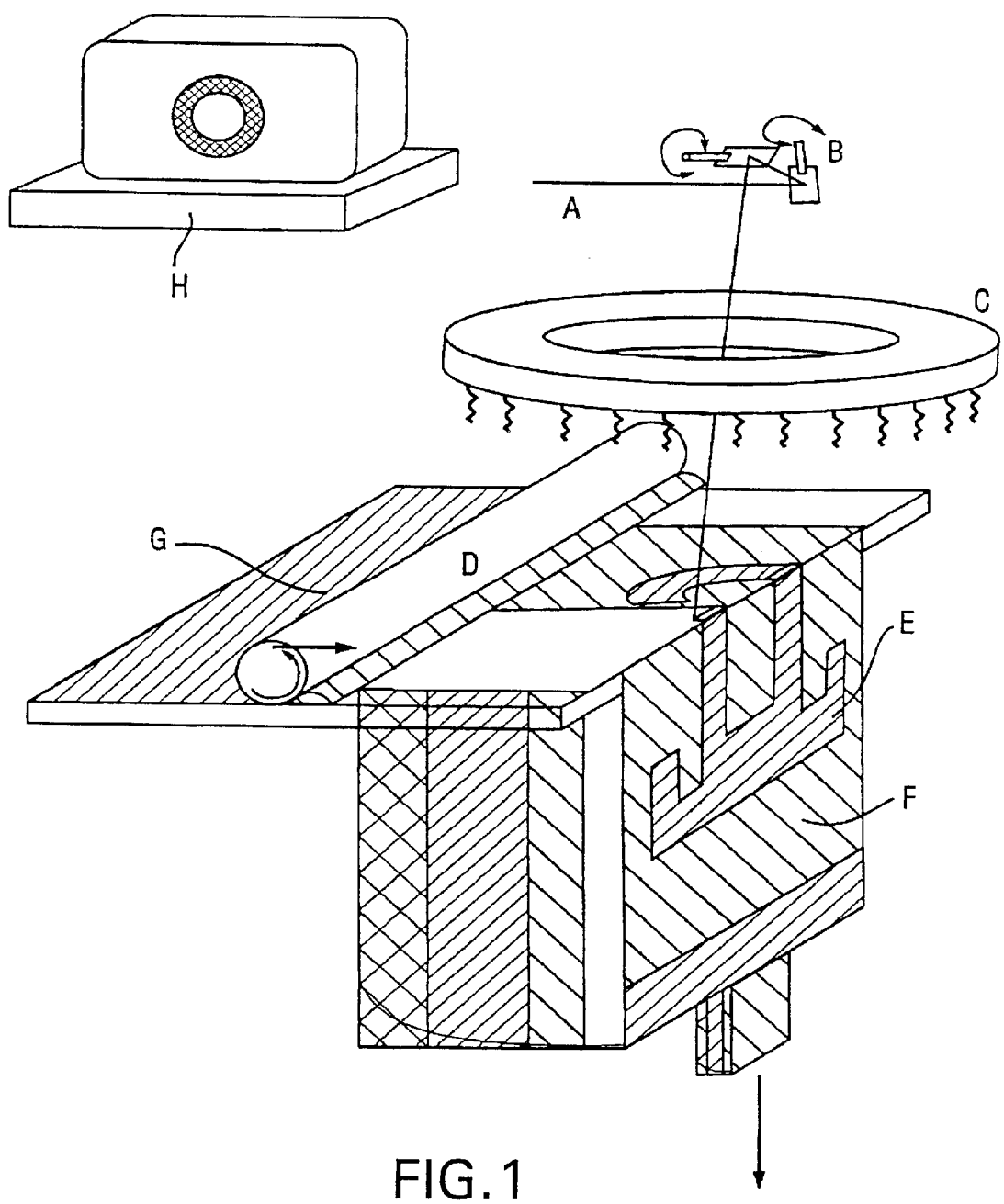
FIG. 1 is a diagram showing a typical apparatus used in the Selective Laser Sintering™ process employed by certain embodiments of this invention. H is a computer control for a laser source A, focused by mirrors B. Heating is provided by a radiant heater C. D is a leveling mechanism for a powder bed F. G is a new layer being added to the part E being produced.

FIG. 1 illustrates an apparatus employed in Selective Laser Sintering™ apparatus. The apparatus includes laser source A, mirrors B, radiant heater C, leveling mechanism D, green part being produced E, powder bed F, new layer G of polymer coated powder, and computer control H. The polymer binder in part E is selectively fused by the action of a low power, rastered, modulated, infrared laser beam A. The preferred type of laser used is dependent on many factors, and in particular the type of powder that is to be sintered. A 25 wattage $CO_2$ laser, typically used to sinter waxes and plastics, generally may be used to sinter the powders of the present invention. The laser beam output of the laser A has a wavelength of 10.60 microns, which is near infrared. In the continuous mode, the laser A can be modulated on or off to selectively produce a laser beam which travels along a specified path. In this manner, the directed laser beam A selectively sinters the powder in the target area to produce the desired sintered layer with the defined boundaries of the desired cross sectional region. This process is repeated layer-by-layer with the individual layers G sintered together to form the green part as shown. It is important to note that in connection with this embodiment the laser beam A fuses only the binder and does not substantially alter or fuse the bioceramic E.

In the illustrated embodiment, the selective fusing is governed by geometric information that is generated by a compatible device at computer control H, such as the CT converter program disclosed with this invention or CAD software. The use of CT scan information permits faithful geometric replication of complex bones to be rapidly and easily prepared by this additive process. In this way, naturally complex bone geometries can be prepared from biocompatible materials that could not be prepared by conventional molding or other fabrication processes. It is also possible to design bones or to modify data from CT scans as might be useful for plastic surgery.

The polymer-bound "green" part E may be post-processed to thermally remove the polymer binder and to sinter and fuse the calcium phosphate powder to prepare bone replicas with a controlled, interconnected porosity. The polymer binder is preferably designed to provide adequate strength to permit handling of the green part, and to debond cleanly without residue. Debonding and sintering can be carried out in a conventional oven that has sufficient capacity to reach the high temperatures required for sintering the ceramic components. Porosity in the final part is a function of SLS™ processing conditions, of oven sintering times and temperatures, and of the original polymer and calcium phosphate type and content in the composite powder.

Post-processing may also encompass infiltrating the implant and then thermally dehydrating the implant. In some current methods of producing prototype parts, water-borne ceramic cementing agents are infiltrated into a polymer bound part previously shaped by laser sintering. The cementing agent is dried and set and the polymer burned out to produce an all-calcium phosphate part. This method of post SLS™ processing has been used to produce other ceramic parts and is described in U.S. Pat. No. 5,284,695. This is generally accomplished at much lower temperatures than post-processing without infiltration. Infiltration can generally accomplished with any inorganic compound or cement generally useful for this purpose. However, where biocompatible implants are desired, it is preferable to infiltrate with calcium phosphate.

Under various circumstances it may also be desirable to sinter the implant thermally and then to infiltrate and thermally dehydrate it. However, infiltration prior to sintering generally results in less shrinkage of the implant.

The polymer binder materials used in the present invention have been developed as thermoplastic binders for ceramic particles, as described in U.S. patent application Ser. No. 08/279,235. The polymeric binders are readily removed from the calcium phosphate compositions by thermal decomposition in oxidizing atmospheres to produce parts that contain only ceramic. In general, the binders are amorphous and polymeric. They are polymers, copolymers or terpolymers having glass transition temperatures above 40° C., and having a melt flow index between about 1 to about 50 g/10 min. at 200° C. and 75 psi extrusion pressure, using the instrument geometry and testing protocols described in ASTM # D1238. Preferred polymer binder compositions include methyl methacrylate and butyl methacrylate. The copolymer of methyl methacrylate and n-butyl methacrylate is particularly preferred as a polymeric binder.

The binders employed in this embodiment of the present invention are different from water soluble binders and slip aids used in conventional ceramics processes in which the binder coated powder is compressed to a shape prior to furnace treatment to remove the polymer and thermally consolidate the ceramic (German, 1990). Such compression is not used in Selective Laser Sintering™ processing; therefore, it is important that coated powders for SLS™ and similar type processing be free flowing at processing conditions.

Additionally, and in a practical sense, water immiscibility of the polymer binder is important. If the binder is too hygroscopic, excess water may create steam during the SLS™ process. This may interfere with or prevent fusion of the binder and substrate into a useful green part. Furthermore, water insoluble polymer binders may permit retention of green shape when infiltrating with water-borne inorganic materials.

Certain binder and binder coating systems may produce a coated particulate that is optimal in size for best performance in the SLS™ process. Particles with diameters from 5 $\mu$m to 25 $\mu$m have been found to spread, level, and sinter well. Depending on the thickness of the powder layer employed, particles as large as 200 $\mu$m (and perhaps larger) can be processed. Lowered bed densities and powder spreading and shear problems may result when particles with diameters smaller than 2 $\mu$m are attempted.

The disclosed emulsion polymer binders (typically containing 40% by weight of polymer solids in water) are mixed with calcium phosphate particles to produce a slurry that contains 5–40 vol % polymer when dried. A small amount, typically <1%, of the emulsion of high molecular weight, water-soluble polymer may be added as a suspension aid to help suspend the inorganic particles that are typically 2–150 $\mu$m. Typical viscosity of the slurry is kept low, approximately 10–100 poise at room temperature, to facilitate spraying of the slurry.

In one example of a preferred coating technique, the slurry of polymer binder emulsion and particulate is spray-dried in a standard NIRO spray drier equipped with a centrifugal atomizer wheel (Vail et al., 1991). The wheel is usually operated at 35,000 rpm causing a fine mist of the slurry mixture to be slung out into a hot air stream. The water in the mist rapidly evaporates to produce solid particles. Particle size in the range of about 25–50 $\mu$m in diameter is preferred. However, by varying the conditions of the spray drying, for example, temperature, feed compositions and atomizer wheel speeds, one can adjust the particle size in either direction (Lefebvre, 1989). The particles obtained are agglomerates of polymer and particulate, as can be seen in FIG. 8. An improperly processed slurry, e.g., where the exit air temperature of the dryer is too low relative to the polymer fusion temperature or where the binder viscosity is too high at the processing temperature employed, may produce a large quantity of smaller, non-agglomerated particles. Such particles do not spread and level as well as the larger agglomerates in the laser sintering processes. For this reason, the $T_g$ or $T_m$ of the polymer binder should be at least 10° C., preferably 15° C. or more, below the exit air temperature of the dryer. Many dryers are operated so that the exit air temperature is near 100–110° C., and for such dryers and drying operations a $T_g$ or $T_m$ below 80–90° C. is preferred.

Another preferred coating technique utilizes a fluidized bed dryer that coats the particulate by fluidizing it in a heated gas stream, then spraying the polymer emulsion into the fluidized bed of particles. This coating technique also works well with the disclosed emulsion polymer binders to give uniformly coated particles. Generally, the disclosed binder system may be used in a variety of coating applications so long as such applications incorporate evaporation of the water vehicle near the normal boiling point of water.

Decomposition of the polymeric binder material may be important because in processes used to produce implants, it is desirable to remove the binder material so all-calcium phosphate parts are obtained. Generally, most organic polymeric binders may be oxidized to carbon dioxide and water in the high temperature furnaces normally used to "fire" or sinter ceramics.

Small amounts of other substances may be added to the binder compositions. For example, chemically similar compounds that do not have the requisite structure for depolymerization may be included to enhance adhesion and other desirable properties. Preferably these monomers make up less than about 10 mole percent of the copolymer composition. Typically, this will amount to only a few percent, e.g., 3–5%, depending on the particular polymer and the desired purpose.

EXAMPLES

Example 1

General Materials and Operating Methods

CHA was obtained as TCP from Monsanto Inc. and phosphoric acid was purchased from Fischer Scientific in 85% concentration. Poly(methyl methacrylate-co-n-butyl methacrylate) copolymer with a Melt Index of 30.9 g/10 min at 75 psi and 200° C. was synthesized as described in the literature (Vail et al., 1994), and used as a polymer binder in Example 2. UCAR 430 Acrylic Polymer Latex (obtained from Union Carbide Corporation) and PMMA emulsion copolymer (Vail et al., 1994) were investigated as polymer binders in Example 3. Inorganic ceramic cement, Cerama Bind™ 542 was obtained from Aremco Products Inc. This inorganic cement, employed in Example 3, is an aluminophosphate material that can react to form phosphate bonded CHA material.

The calcium phosphate powders were ground by a Szegvary attritor system, type 1HSA, prior to being mixed with polymer for SLS™ processing. Acceptable ranges in particle size were from 20 to 100 microns in diameter with 30 to 50 microns being preferred.

The mercury porosimeter, Poresizer 9320 from Micromeretics was used to determine the surface area of the powder. The powder samples were heated to expel the absorbed moisture and then stored in a desiccator until analyzed. The sample in a penetrometer was initially evacuated to 25 $\mu$Hg. Mercury was then admitted and pressure was increased up to 30,000 psi which is capable of measuring pore size of 0.006 $\mu$m. A contact angle of 130° was assumed in the calculation of pore size. The particle size distributions of powders were measured by a Coulter Multisizer.

Samples of polymer coated substrates were prepared by spray drying a slurry of emulsion copolymer and calcium phosphate powder according to the following equations that determine the amount of each ingredient:

$$m_E = m_s \left( \frac{x_p}{x_E(1-x_p)} \right) \quad (12)$$

$$m_w = \frac{m_s}{x_E x_s (1-x_p)} (x_E(1-x_s+x_s x_p) - x_p x_s)$$

where $$x_p = \frac{(\rho_p \phi_p)}{(\rho_p \phi_p + (1-\phi_p)\rho_s)}$$

where $m_E$ is the required amount of emulsion, $m_s$ the amount of powder to be coated, $m_w$ the amount of water to be added, $x_p$ is the mass fraction of polymer in the resulting sample, $x_E$ the solids mass fraction of the emulsion polymer, $x_s$ the total solids mass fraction of the final slurry, $\phi_p$ is the mass fraction of the copolymer, pp is the density of the polymer, and $\rho_s$ is the substrate density.

Polymer binders were deposited on the calcium phosphate powders by spray drying a slurry of the calcium phosphate powder and the polymer emulsion employing either a bench scale Pulvis Mini Spray Dryer or a pilot plant scale NIRO Spray Dryer, equipped with a centrifugal atomic wheel. Operating conditions for the NIRO Spray Dryer were 30,000 rpm and an exit gas temperature of 110° C. Alternatively, mixtures were formed by physically mixing polymer binders, which had been spray dried, with the dried calcium phosphate powder.

SLS™ Processing

The SLS™ machine used for this work was a Model #125 (DTM Corp., Austin, Tex.). Polymer coated powders produced by the spray coating method were processed by SLS™ to fabricate the desired green shapes according to the following method. The free-flowing polymer coated powder was loaded into the SLS™ machine for processing. The operating environment temperature was biased to heat the powder bed to just below the glass transition temperature, $T_g$, of the binder, ~90° C. This corresponds to a setting of 104° C. on the temperature controller. This controller operated on a temperature feedback signal supplied by an infrared sensor (emissivity=0.90). The sensor indicated the temperature at the powder surface. Overbiasing of the environment temperature was prevented by a thermocouple located just below the surface of the radiant heater. At equilibrium conditions this thermocouple indicated a temperature of ~119° C. These readings were machine dependent as well as material dependent. The powder bed temperature and the operating environment were allowed to equilibrate for at least 1 hr. The environmental atmosphere was maintained semi-inert ($O_2$<8%) by $N_2$ purge.

Sintering of the polymer coated powder was accomplished using a modulated, $CO_2$ laser beam using scanning conditions prescribed in the actual experiments. The parameters, except the layer thickness, can be combined to give the applied energy density defined as:

$$A_N = \frac{P}{BS * SCSP} [=] \frac{cal}{cm^2} \quad (13)$$

where $A_N$ is the applied energy density, P the laser output power, BS the beam scan speed, and SCSP the scan line spacing. When expressed in the given units this number had values generally less than 10.0 cal/cm². Parts exhibiting acceptable green strengths were produced with $A_N$>0.5 cal/cm². This lower limit appeared to be constant for most material systems. Typically, parts were produced with $A_N$ values of about 2 to 2.5.

Processing CT Scan Data for SLS™

The CT data image of human temporal bones was received from a GE 9800 CT scanner as a series of slices, nominally 1.5 mm thick. Each slice consisted of a raster image of the temporal bone; the resolution of each image was 256×256 volume elements, or voxels. Each voxel was 2.5 mm² and was represented as a floating point number indicating the average density of the tissue at that voxel location. The density is measured in Hounsfeld units, representing the ratio of the tissue density to the density of water. Density values ranged from −1000 to 3095. The SLS™ process required boundary information rather than interior density data; therefore, a conversion process was necessary.

A computer program was written to convert the raster images to contour images of the temporal bone slice in each plane by specifying a minimum threshold density below which the data could be ignored. A source code listing of this program is appended at the end of this specification. The threshold value was selected manually by a CT technician and provided as input. The program then scanned each row in the raster image to locate changes in density that crossed the threshold value provided. These changes represent the bone contour outline. Each voxel at which the threshold crossing is detected is converted to a laser toggle point location by simple translation and scaling transformations. The parameters for this conversion are based on the known size of the sample. The toggle point information was then written in a file in the correct format for direct processing by the SLS™ machine.

In cases where the thickness did not coincide with the thickness required for the SLS™ process (typically 0.005 to 0.01 inches), the SLS™ control compensated for this by either skipping layers (for thinner layers) or replicating layers (for thicker layers).

The thresholding software was implemented in the C programming language on a Sun Microsystems SparcStation 2 workstation with the UNIX operating system. The implementation is independent of the hardware and could be ported to other stations.

Example 2

Bioceramics from CHA Derived Powders

This experiment illustrates the fabrication of complex and delicate bone shape parts from CT data using a Selective Laser Sintering™ process. In order to make denser porous implants, calcium metaphosphate powder that has been mixed with polymer binder and SLS™ processed was either heated at high temperatures for long periods of time, a procedure that increased shrinkage and geometric inaccuracies, or heated at lower temperatures for shorter periods of time to lightly sinter the part followed by infiltration with a calcium phosphate solution, drying, and refiring at a lower temperature to produce a calcium ultra-phosphate glass-bound calcium metaphosphate structure. Alternatively, a part made from a calcium phosphate powder that contained a higher Ca/P ratio than CMP, e.g., tromelite (referred to herein as "35CaP"), was infiltrated with a calcium phosphate solution and fired to produce a calcium metaphosphate-bound structure that had better physical properties, low shrinkage and higher density. It is also possible to infiltrate with a calcium phosphate solution prior to the first heating to remove polymer and sinter the part.

Figure 4:
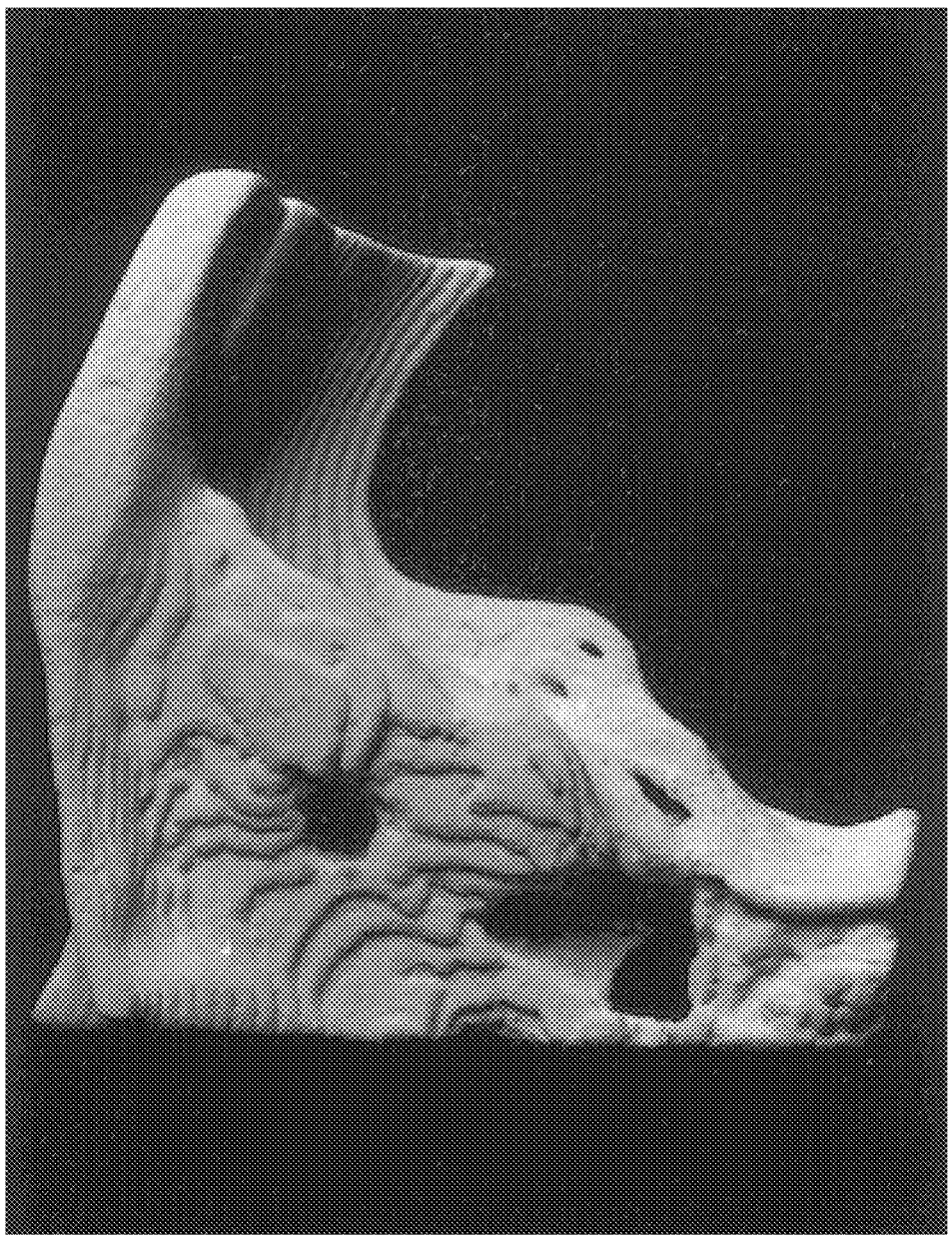
FIG. 4 is a photograph of an SLS™ processed craniofacial implant fabricated from CMP powder.

Complex bone shapes, such as that shown in FIG. 4, required green strengths near 150 psi to permit ordinary handling. This craniofacial image, composed of 27 different layers, was created from CT scans of a human temporal bone (Levy, 1992). This part was approximately four inches long and one and half inch thick with well defined cavities.

Powder Preparation (1) Calcium metaphosphate ($\{Ca(PO_3)_2\}_n$, "CMP")

CHA (251 g) was reacted with a solution of 85% phosphoric acid (403 g) in water (150 g) at room temperature, pursuant to equation 14. The prepared paste was dried at room temperature and then heated to 150–200° C., pursuant to equation 15.

$$Ca_5(OH)(PO_4)_3 + 7H_3PO_4 \xrightarrow{\text{room temp.}} Ca(H_2PO_4)_2 \cdot H_2O \quad (14)$$

$$Ca(H_2PO_4)_2 \cdot H_2O \xrightarrow{150-200°\ C.} Ca(H_2PO_4)_2 + H_2O \quad (15)$$

The reaction product was confirmed by the x-ray diffraction analysis. Powder that was heated to 150° C. exhibited the x-ray diffraction pattern of a mixture of $Ca(H_2PO_4)_2$ and $Ca(H_2PO_4)_2 \cdot H_2O$. This powder was further dehydrated to β-calcium metaphosphate (CMP), pursuant to equation 16, which is theoretically composed of 28 wt % of CaO and 726 of $P_2O_5$ and reported to have an average chain length of 10,000 (Corbridge, 1990). The x-ray diffraction pattern of CMP made by the described method is compared to the standard pattern in FIG. 3B.

$$Ca(H_2PO_4)_2 \xrightarrow{600-700°\ C.} Ca(PO_3)_2 + 2H_2O \quad (16)$$

(2) Calcium pyrophosphate ($Ca_2P_2O_7$, "CPP")

CPP was prepared from reacting CHA (251 g) with 85% phosphoric acid (196 g) in a manner analogous to that described for the preparation of CMP.

$$Ca_5(OH)(PO_4)_3 + 2H_3PO_4 \xrightarrow{150-200°\ C.} CaHPO_4 2H_2O + H_2O \quad (17)$$

$$2CaHPO_4 \cdot 2H_2O \xrightarrow{700-750°\ C.} Ca_2P_2O_7 + 5H_2O \quad (18)$$

(3) Calcium phosphate with 35 wt % of CaO ("35CaP")

Figure 3A:
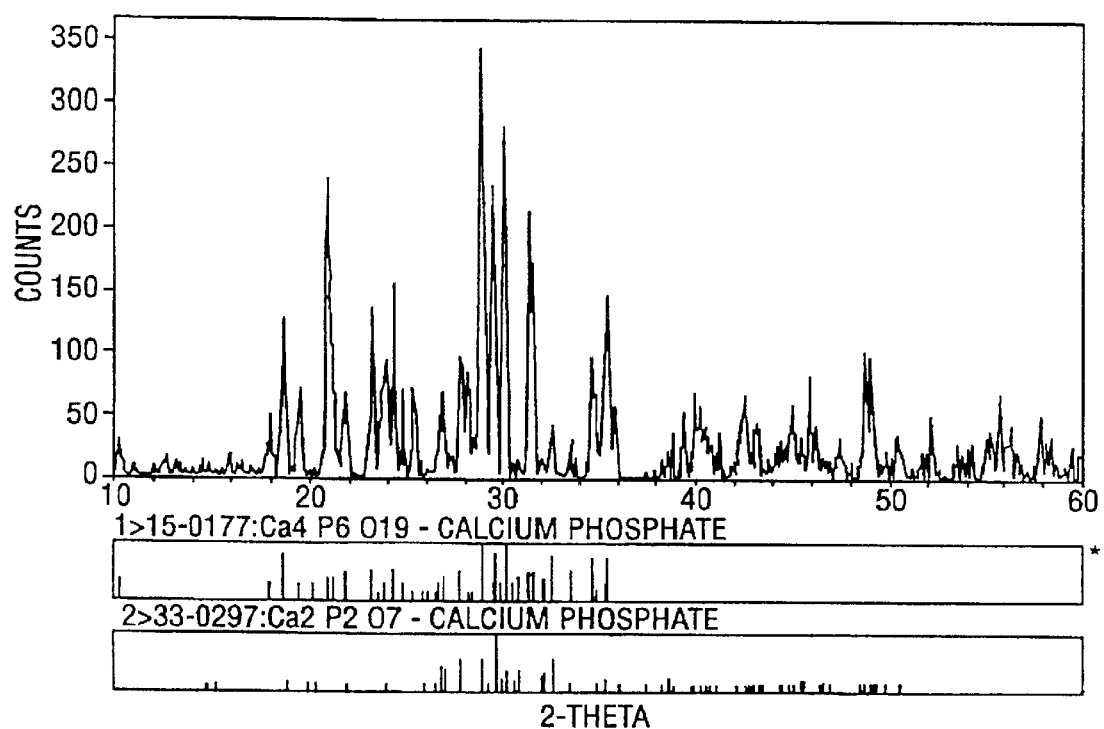
FIG. 3A is an x-ray diffraction pattern for calcium phosphate with 35. by weight of calcium oxide powder. This pattern closely matches that of tromelite, $Ca_4P_6O_{19}$ (upper small box)

CHA (251 g) was reacted with 85% phosphoric acid (251 g) X-ray diffraction pattern of this powder, as shown in FIG. 3A, was identified by JADE x-ray peak identifying program as mixture of major phase of $4CaO.3P_2O_5$ and minor phase of CPP, "tromelite".

(4) CPP with 1 wt. % of $Na_2O$ ("1NaCPP")

The prepared CPP powder was mixed with 1 weight percent of $Na_2O$ (by addition of 1.7% by weight of $Na_2CO_3$) to depress the melting temperature in order to study the influence of surface area of the powder on green strength. 1NaCPP was thermally coalesced at 1020° C. and then ground in the attritor. The ball milling time was controlled to have different particle size and consequently surface area. Three samples of pore surface area, 1.8, 1.4, and 1.1 m²/g, were measured by mercury porosity.

In the powder preparation step, a firing temperature of 900° C. was sufficient to coalesce CMP, melting point of 985° C. However, for 35CaP powder, which had a higher melting temperature 900° C. was not high enough to coalesce the powder. The resulting powder had a very high surface area but the green parts had only 40 psi strength with 15% by weight of polymer binder. This reasoning was verified when CPP powder, fired at 1300° C. for 2 hours, then ground in the attritor and classified to a mean diameter of 30 μm, showed good green strength, whereas the powder fired at 900° C., ground to a mean diameter of 2 μm, showed barely any green strength. Also, 1NaCPP powder with a surface area of 1.8 m²/g exhibited poor green strength, while the powder with a surface area of 1.4 m²/g showed very good strength. Both powders were mixed with 15% polymer binder by weight.

SLS™ Processing

The appropriate powder was physically mixed with 15% by weight (30% by volume) of spray dried polymer, poly (methyl methacrylate-co-n-butyl methacrylate) copolymer, and SLS™ processed with the conditions shown in Table 1.

TABLE 1

| SLS Parameters | | | | |
| --- | --- | --- | --- | --- |
| Power (W) | Scan Space (mil) | Beam Speed (ips) | Layer thickness (mil) | Bed Temp. (° C.) |
| 7.5 | 5 | 25 | 5 | 90 |

The SLS™ processed CMP green parts had a density of about 0.91±0.03 g/cm³, 33% of the theoretical density, with the fracture strength of 130±20 psi. This was sufficient to permit rough handling of complex bone shapes, such as that shown in FIG. 4.

However, 35CaP green parts had a density of 0.83 g/cm³ with a fracture strength of 40±10 psi. This relatively low strength of the latter parts was attributed to smaller particle size and, consequently, higher surface area of this powder than that of the CMP powder.

Post Processing

Three methods to process the implants after they have been formed by laser sintering are: (1) thermal sintering, (2) thermal sintering to set implant and then infiltration/dehydration/sintering, and (3) no thermal sintering prior to infiltration/dehydration/sintering. The first method involved firing the implant for several hours at sintering temperatures, roughly 800–1600° C., depending on the calcium phosphate composition used. This approach produced the highest strength materials. However, the firing step caused the part to shrink, which may not be desirable for construction of an accurate facsimile bone structure from geometric information obtained from patient CT data. Furthermore, the shrinkage was not isotropic. Linear shrinkage in thickness was much larger than that in width or length, due to the nature of layer-wise construction of parts in SLS™ process.

Figure 5:
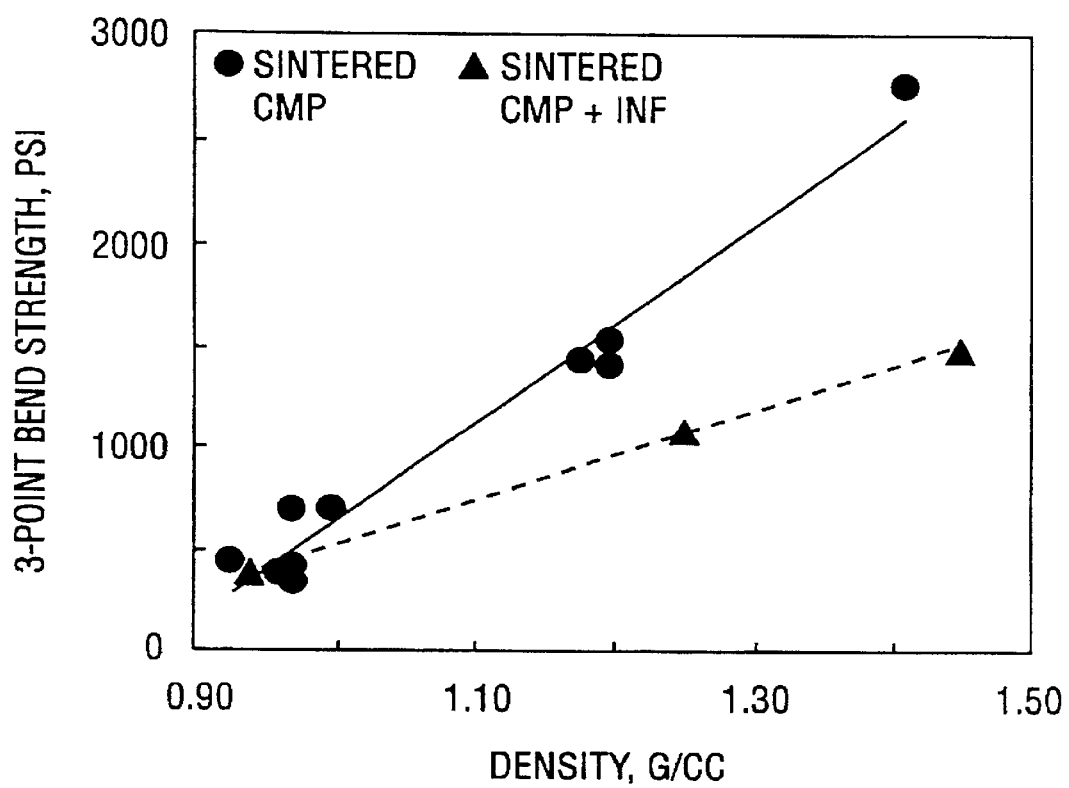
FIG. 5 is a graph demonstrating the effect of the density of a fired and a infiltrated part on the modulus of rupture (three point bending strength).

The second approach was accomplished either by sintering the implant for a reduced period of time, and then infiltrating and dehydrating the implant and heating to the melting point of the infiltrant to sinter the part. This approach allowed the implant's density and strength to be increased relative to an implant with the same sintering conditions but no infiltrant. The implant also shrank much less than in the direct thermal sintering approach. However, the implant exhibited less green strength as a function of density, as shown in FIG. 5.

The third approach to reduce shrinkage is to infiltrate the implant and then thermally dehydrate and sinter it without a previous firing step (U.S. Pat. No. 5,284,695). This may decrease the amount of shrinkage and green strength even more.

Another issue that affects the choice of post-processing method is the resorbability of implant desired. The resorbability is a function of the density. Therefore, by adjusting density, perhaps by filling the pores with calcium phosphate, the resorbability of the implant can also be adjusted.

Due to the severe restriction imposed on the selection of a cement for biomedical applications, a calcium phosphate solution was chosen as the infiltrant in this experiment. For effective penetration through the pore, the calcium phosphate should to be dissolved completely in a biologically acceptable media.

(1) Thermal Sintering Method

The green parts were fired up to sintering temperature to remove the polymer and subsequently sinter the calcium phosphate. The temperature was raised at an average rate of 16° C./min up to 500° C. and then raised slowly to 880° C. The parts were held at 880° C. for 2 hours and cooled down slowly. During the firing, the parts were kept in lightly packed CHA powder to help maintain the shape and provide even heat distribution to reduce curling. CHA was chosen as the packing material due to its low bulk density, less than 0.5 g/cm³, and high melting temperature.

CMP green parts were fired at 880° C. for 2 hours. The fired CMP parts showed a 3 point bending strength of about 400 psi and a density of about 0.97 g/cm³, corresponding to a 17% volume shrinkage. A strength of about 2700 psi was obtained by firing a CMP part at 940° C. for 1 hour with a density of about 1.4 g/cm³.

(2) Infiltration/Dehydration/Sintering after Thermal Sintering Method

Parts were sintered as described above, and then infiltrated with a calcium phosphate solution. Calcium phosphate paste was prepared by mixing CHA and phosphoric acid which was then diluted with water to form a slurry. The prepared slurry was dissolved in boiling water. It was found that 15 g of CHA with 60 g of 85% phosphoric acid was a good composition when dissolved in boiling water to make about 120 ml of solution.

Infiltration was performed mainly by capillary action by placing the implant in the solution. After the pores were saturated with infiltrant, the parts were taken out of the solution and allowed to dry at 50° C. and then fired at the appropriate temperature according to the expected final Ca/P ratio. It was found that when the pores were saturated upon infiltration, the resulting weight gain was inversely proportional to the initial density.

The polymer free parts with a density of about 0.97 g/cm³ were infiltrated as described earlier. For the CMP parts, a first infiltration resulted in 31±2% weight gain after firing 725° C. and strength of 1100 psi and subsequent infiltration increased the density about 50% and strength about 1500 psi. Strength vs. density data are shown in FIG. 5. Further infiltration caused the parts to melt and deform inhomogeneously at 725° C., which could indicate existence of a Ca/P concentration gradient through the part. This also lowered the strength of the part. The fractured surface of this part showed randomly distributed vitrified parts. It is believed that infiltrant filled up the pore and formed a phosphate glass.

The formation of phosphate glass was verified in a separate experiment. In this experiment, the calcium phosphate solution was heated to 600° C. where it formed a nonporous transparent glass that contained 15.7% CaO. As additional proof, the infiltrated part was ground to a powder for x-ray diffraction analysis. There was no significant difference in x-ray patterns before and after infiltration. This indicates that no new crystalline phase had been formed.

A 35CaP green part was fired for 2.5 hours at 880° C. to achieve a lightly sintered structure. The structure showed a 40% weight gain upon first infiltration with a calcium phosphate solution due to its lower density. This part was dried and then heated to 7250 for longer than 6 hours. Further infiltration increased the strength to about 4200 psi and a relative density of 57%, density of 1.6 g/cm$^3$.

Figure 3B:
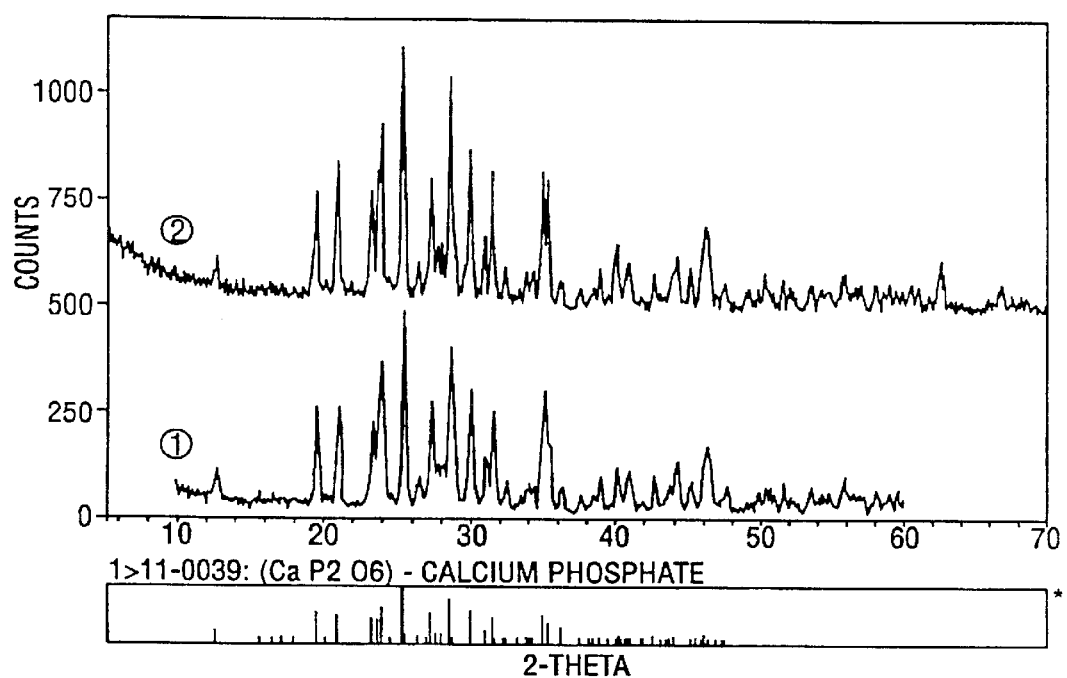
FIG. 3B is an x-ray diffraction pattern for CMP powder (1) as directly prepared and (2) as prepared from a fired 35CaP part that was infiltrated with a calcium phosphate solution and fired again.
Figure 6A:
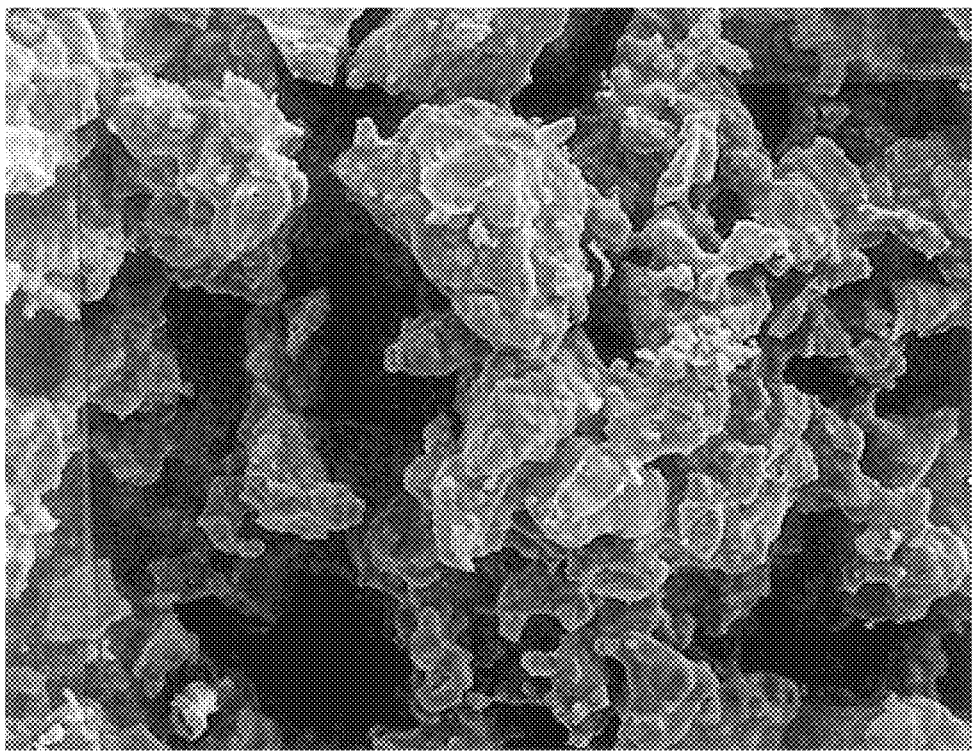
FIG. 6A is a scanning electron micrograph of a porous surface after firing, shown at 200 times magnification.
Figure 6B:
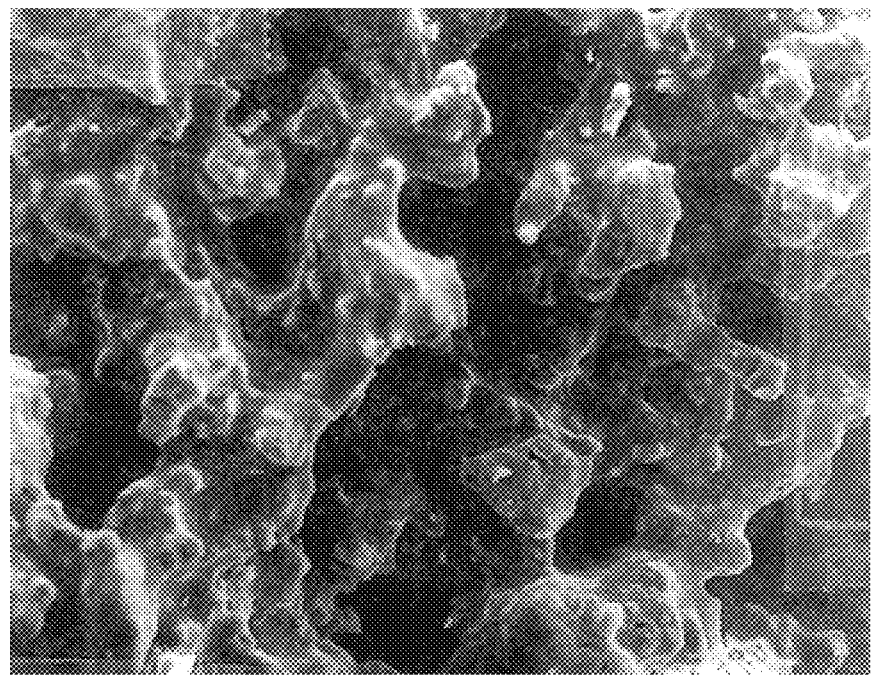
FIG. 6B is a scanning electron micrograph of a porous surface after firing and infiltration, shown at 200 times magnification.

X-ray diffraction analysis indicated that the initial powder, which was a mixture of major phase of $4CaO.3P_2O_5$ and minor phase of CPP, was converted to calcium metaphosphate after post processing. FIG. 3B shows this phase transformation. The morphology of the fired and infiltrated fracture surface are shown in FIGS. 6A and 6B. Infiltration caused more necking between the grains. The pores were well interconnected and the pore size was approximately larger than 50 μm.

Example 3

Implant Fabrication with Hydroxyapatite

This experiment details preliminary efforts to fabricate implants from calcium hydroxyapatite reacted with orthophosphoric acid. The strengths of the sintered materials in this example were found to be very low.

The failure of this experiment has been ascribed to the lower temperatures of the reaction of the CHA and orthophosphoric acid. In this case, the calcium phosphates were not converted to the more stable meta- and pyro-phosphates but were instead hydroxyapatite hydrates. When these compositions were processed with laser sintering, they were converted to the meta- and pyro-phosphates with the concomitant production of steam. This water was very detrimental to the formation of the implants. Therefore, implants with acceptable green strengths, densities and porosities were not produced.

This example demonstrates that the calcium phosphates of the present invention must be prepared at high enough temperatures prior to SLS™ processing to not decompose during such processing to produce water.

Experimental

To determine the required amount of polymer binder, the coated powder was heated in air to 150° C. to fuse the polymer. Afterwards, the powder was cooled and qualitatively examined. More than 20% (45 vol. %) of UCAR 430 was required to produce a cake that barely permitted handling. While polymethyl methacrylate copolymer coated materials showed better properties at 20% coating, cakes were still easily crumbled. These problems were attributed to the high surface area of the finely divided CHA powder. In an attempt to modify surface area, CHA (50 g) was reacted with orthophosphoric acid ($H_3PO_4$) (100 ml, 5M), and heated to 150° C. to form a cake. The cake was then ground back to a finely divided powder. The morphology of the reacted CHA powder is shown in FIG. 7. The powder was spray dried with 14% by weight (30% by volume) of polymethyl methacrylate polymer and examined. The oven sintered cake showed significantly improved strengths, enough to permit rough handling.

Based on the oven tests, the coating of the CHA powders with the 14% of PMMA copolymer was scaled up by using an Anhydro Laboratory Spray Dryer (Vail et al., 1991). The operating conditions were as follows:

Slurry solids content: 45 wt. %
Inlet temperature: 175° C.
Outlet temperature: 110° C.
Atomizer speed: 30,000 rpm FIG. 8 shows the scanning electron micrograph of a polymer coated powder. Spray dried powders were SLS™ processed employing the operating conditions presented in Table 2.

TABLE 2

| Operating conditions of SLS ™ machine. | | | | |
|---|---|---|---|---|
| Power (W) | Bed Temp. (° C.) | Layer Thickness (mil) | Scan Space (mil) | Scan Speed (inch\sec) |
| 5 | 120 | 8 | 5 | 15 |

SLS™ processed parts were infiltrated with a phosphoric acid based inorganic cement. High surface tension was observed upon infiltration which prevented effective penetration by the cement, Cerama Bind™. Methanol and Witcolate D51-51 surfactant (Witco Corporation) were used to reduce the surface tension. Infiltrated green parts were dried for 5 days under ambient conditions. Upon drying, the parts were cured in the oven, at 200° C., raised from ambient temperatures at a rate of 50° C./hr. As a final step, green parts were fired up to 700° C. in the furnace for 2 hours to burn off the polymer.

Results and Conclusions

Oven tests showed that parts made with polymer coated non-reacted CHA could not achieve acceptable green strengths. Low bulk density, due to very large specific surface area caused by very small particle sizes and large porosity, is believed to be the reason for this behavior, although the hygroscopic nature of the CHA could be a contributing factor.

Figure 9:
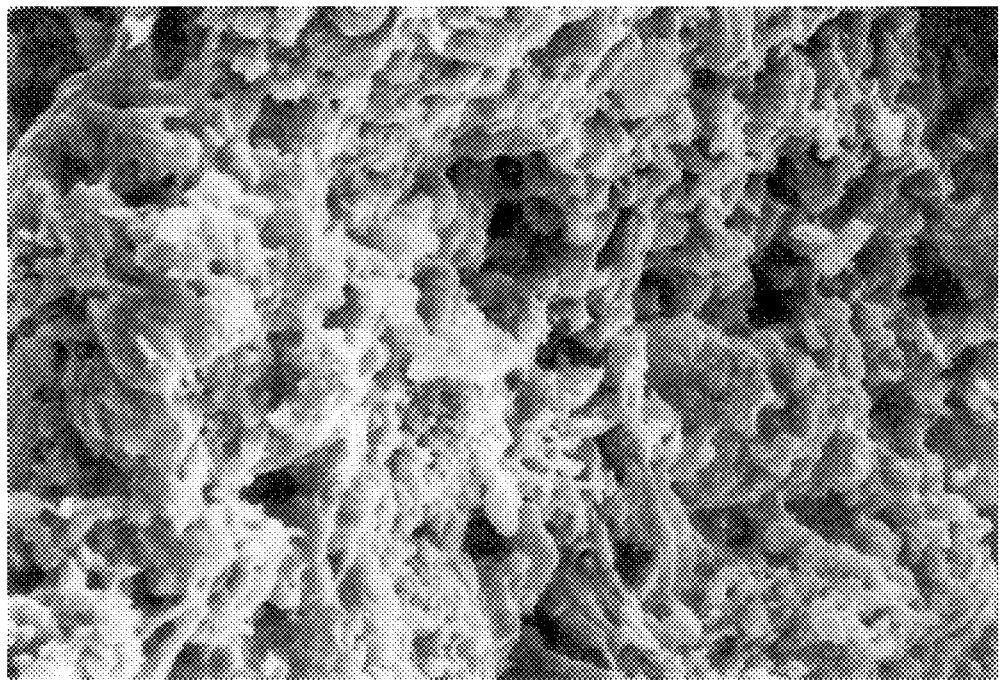
FIG. 9 is a scanning electron micrograph of a sintered surface at 800 times magnification.

While CHA in its pure form has a bulk density of less than 0.4 g/cm$^3$, CHA reacted with 5M phosphoric acid shows increased density to over 0.7 g/cm$^3$. SLS™ processed parts made of reacted CHA had sufficient strengths for rough handling as oven tests of the sintered cakes predicted. The strengths of post-processed bioceramic parts were even higher. FIG. 9 shows a fractured surface of a part that was post processed and fired.

While the compositions and methods of this invention have been described in terms of preferred embodiments, it will be apparent to those of skill in the art that variations may be applied to the systems, compositions, methods and in the steps or in the sequence of steps of the methods described herein without departing from the concept, spirit and scope of the invention. For example, it will be apparent that certain agents which are chemically, compositionally and functionally related may be substituted for the agents described herein where the same or similar results may be achieved. All such similar substitutes and modifications apparent to those skilled in the art are considered to be within the spirit, scope and concept of the invention as defined by the appended claims.

BIBLIOGRAPHY

U.S. Pat. No. 3,379,541 to Tuvell (1968).
U.S. Pat. No. 3,913,229 to Driskell et al. (1975).
U.S. Pat. No. 4,046,858 to Barsa et al. (1977).
U.S. Pat. No. 4,048,300 to Tomlinson et al. (1977).
U.S. Pat. No. 4,097,935 to Jarcho (1978).
U.S. Pat. No. 4,113,500 to Ebihara et al. (1978).
U.S. Pat. No. 4,131,597 to Bluethgen, et al. (1978).
U.S. Pat. No. 4,135,935 to Pfeil et al. (1979).
U.S. Pat. No. 4,149,893 to Aoki et al. (1979).

U.S. Pat. No. 4,207,306 to Jarcho (1980).
U.S. Pat. No. 4,222,128 to Tomonaga et al. (1980).
U.S. Pat. No. 4,223,412 to Aoyagi et al. (1980).
U.S. Pat. No. 4,224,072 to Steward (1980).
U.S. Pat. No. 4,230,455 to Hidaka et al. (1980).
U.S. Pat. No. 4,274,879 to Irvine (1981).
U.S. Pat. No. 4,308,064 to Takami et al. (1981).
U.S. Pat. No. 4,324,772 to Conn et al. (1982).
U.S. Pat. No. 4,330,514 to Nagai et al. (1982).
U.S. Pat. No. 4,673,355 to Farris et al. (1987).
U.S. Pat. No. 5,076,869 to Bourell et al. (1991).
U.S. Pat. No. 5,284,695 to Vail and Barlow (1994).
U.S. patent application Ser. No. 08/279,235 filed Jul. 22, 1994 by Barlow et al.
Albee et al. *Ann. Surg.*, 71:32–39, (1920).
Barlow 3rd *International Conference on Rapid Prototyping*, pp. 73–79, (1992).
Bhashar et al. *Oral Surg.*, 31:282–289, (1971). Bovey et al. *Emulsion Polymerization*, Interscience Publishers, Inc., 1, (1955).
Cameron et al. *J. Biomed. Materials Res.*, 11:179–186, (1977).
Capano *The chemical synthesis and biomedical and dental applications of the first truly successful in vivo replacements for bones, teeth, and similar materials*, Ph.D. Thesis, University of Texas at Austin, (1987).
Corbridge *Phosphorous: an outline of its chemistry, biochemistry and technology*, Elsevier, 224, (1990).
Cutright et al. *Oral Surg.*, 33:850–856, (1972).
deGroot *J. Biomaterials*, 1:47–50, (1980).
Ferraro et al. *J. Dent. Res.*, 58-A:410, (1979).
German *Powder Injection Molding*, Metal Powder Industrial Federation, (1990).
Hattori et al. *J. Am. Ceram. Soc.*, 73(6):1803, (1990). Hill et al. *Amer. J. Sci.* 242:457–477, 542–562, (1944).
Holmes *Plast. Rec. Surg.*, 63:626–633, (1979).
Hulbert et al. "History of Bioceramics", in *Ceramics in Surgery*, Vincenzini, ed., Elsevier: Amsterdam, 3–27, (1983).
Jarcho et al. *J. Materials Science*, 11:2027–2035, (1976).
Jarcho et al. *J. Bioeng.*, 1:79–92, (1977).
Koster et al. *Langenbeck's Arch. Chir.*, 343:172–181, (1977).
Koster et al. *Langenbeck's Arch. Chir.*, 341:77–86, (1976).
Lefebvre *Atomization and Sprays*, Hemisphere Publishing, (1989).
Levy et al. *Am. J. of Neuroradiology*, 15:473–477, (1994).
Levy et al. *Solid Freeform Fabrication Symposium Proceedings*, 3:161–173, (1992).
McIntosh et al. *Anal. Chem.*, 28(9):1424–1427, (1956).
Nelson et al. *J. Oral & Maxillofacial Surg.*, 51:1363–1371, (1993).
Nielson, A.; *Acta Chir. Scandanav.*, 91:17–27, (1944).
Peltier et al. *Ann. Surg.*, 146:61–64, (1957).
Vail et al. *J. Appl. Polyin. Sci.*, 52:789–812, (1994).
Vail et al. *Solid Freeform Fabrication Symposium Proceedings*, 3:124–130, (1992).
Vail et al. *Solid Freeform Fabrication Symposium Proceedings*, 2:195–205, (1991).
Van Wazer *Phosphorous and Its Compounds*, Interscience Publisher, 1:517–522, (1958).
Yoshihiro *Shika Rikogaku Zasshi*, 16:196–202, (1975).

```
/****************************************************************
#      Section Name        :newimage.c                *

#      Resp. Engineers     :Suman Das and Sashidhar Guduri

#      Description         :Program to convert CT scan data to
#                           toggle point format
*****************************************************************
#      Included Functions

*****************************************************************
#      Current SCCS Version:1                         *
*****************************************************************
#      Revision History

#      1.1 on 5/2/1992                                *

****************************************************************/
#include <stdio.h>
#define TRUE  1
#define FALSE 0
main(argc,argv)                                                      main
int argc;
char *argv[];
{
        unsigned short inbuf[512];
        unsigned short outbuf[1024];
        FILE *infp;
        int i;                        /* pixel count */
        int j;                        /* scanline count */
        int k;
        int flag;
        unsigned short eol = 0xfffe;
        flag = FALSE;
        if (argc == 2)
          {
          if((inf = fopen(argv[1],"rb")) == NULL)
            {
```

-continued

```
            fputs("open failed",stdout);
            exit(0);
            }
        for(j=0;j<512;j++)
            {
            k = 0;
            fread(inbuf,sizeof(unsigned short),512,infp);
            for(i=0;i<512;i++)
                {
                if(inbuf[i] > 1224)
                    {
                    if(flag == FALSE)
                        {
                        outbuf[k] = j;
                        outbuf[k+1] = i;
                        k = k + 2;
                        }
                    flag = TRUE;
                    }
                else
                    {
                    if(flag == TRUE)
                        {
                        outbuf[k] = j;
                        outbuf[k+1] = i;
                        k = k + 2;
                        }
                    flag = FALSE;
                    }
                }
            fwrite (outbuf, sizeof (unsigned short), k, stdout);
            }
        fwrite (&eol, sizeof (unsigned short), 1, stdout);
        fclose(infp);
        }
}
```
...main

What is claimed is:

1. An implant produced by
   a. forming a mixture of a calcium phosphate composition and a binder;
   b. selectively fusing the binder to form an implant green part; and
   $c_1$. infiltrating the implant green part; or
   $c_2$. sintering the implant green part to form an implant,
   wherein
   the calcium phosphate composition does not decompose to produce water during step b, and
   the implant
   replicates a naturally complex bone geometry,
   has a complex three-dimensional shape with a well-defined cavity, the cavity replicating internal complex bone geometry,
   has a controlled, interconnected porosity, and
   has a mole ratio of calcium to phosphorus of 0.5 to 1.

2. An implant produced by selectively fusing a calcium phosphate composition with a binder to form an implant green part; and sintering the implant green part to form an implant,
   wherein
   the calcium phosphate composition does not decompose to produce water during fusing, and
   the implant
   replicates a naturally complex bone geometry,
   has a complex three-dimensional shape with a well-defined cavity, the cavity replicating internal complex bone geometry,
   has a controlled, interconnected porosity, and
   has a mole ratio of calcium to phosphorus of 0.5 to 1.

3. The implant of claim 2 further including infiltrating the green part or the implant.

4. An implant produced by selectively fusing a calcium phosphate composition with a binder to form an implant green part; infiltrating the green part, and sintering the green part to form an implant,
   wherein
   the calcium phosphate composition does not decompose to produce water during fusing, and
   the implant
   replicates a naturally complex bone geometry,
   has a complex three-dimensional shape with a well-defined cavity, the cavity replicating internal complex bone geometry,
   has a controlled, interconnected porosity, and
   has a mole ratio of calcium to phosphorus of 0.5 to 1.

5. An implant produced by
   a. forming a mixture of particles of a calcium phosphate composition and a binder;
   b. forming a layer of the mixture;
   c. selectively fusing the binder;
   d. repeating steps b. and c. a desired number of times to form a plurality of layers, wherein each layer is fused to adjacent layers to form the implant green part; and
   $e_1$. infiltrating the implant green part; or
   $e_2$. sintering the implant green part to form an implant,
   wherein
   the calcium phosphate composition does not decompose to produce water during step c, and
   the implant
   replicates a naturally complex bone geometry, has a complex three-dimensional shape with a well-defined cavity, the cavity replicating internal complex bone geometry, has a controlled, interconnected porosity, and has a mole ratio of calcium to phosphorus of 0.5 to I.

6. The implant of claim 1, 2, 4, or 5 wherein the calcium phosphate composition is prepared at a temperature greater than about 200° C.

7. The implant of claim 1, 2, 4, or 5 wherein the binder is selectively fused with a laser beam.

8. The implant of claim 1, 2, 4, or 5 or wherein the binder is selectively fused with a thermal mask system.

9. The implant of claim 1, 2, 4, or 5 wherein the binder is selectively fused to form a desired geometrical shape.

10. The implant of claim 1, 2, 4, or 5 wherein the binder is a polymer binder.

11. The implant of claim 10, wherein the polymer binder has a $T_g$ of between about 40° C. and about 100° C., and a melt flow index of between about 1 and about 50 g/10 minutes at 200° C. and 75 psi extrusion pressure.

12. The implant of claim 10 wherein the polymer binder comprises a homopolymer, copolymer, or terpolymer of methyl methacrylate.

13. The implant of claim 1, 2, 4, or 5 wherein the binder is a liquid binder.

14. The implant of claim 1, 2, 4, or 5 wherein the binder is coating calcium phosphate particles.

15. The implant of claim 2 or 4 wherein the binder is applied to the calcium phosphate composition as a spray.

16. The implant of claim 1, 2, 4, or 5 wherein the calcium phosphate composition is calcium metaphosphate, calcium pyrophosphate, calcium phosphate with from about 25 percent to about 45 percent by weight calcium oxide, or calcium phosphate with from about 0.5 to about 2 percent by weight sodium oxide.

17. The implant of claim 1, 3, 4, or 5 wherein the infiltrating is with a calcium phosphate solution.

18. The implant of claim 1, 2, 4, or 5 wherein the binder is selectively fused by spraying of a liquid binder and solvent.

19. An implant produced by a. forming a mixture of a calcium phosphate composition and a binder;

b. selectively fusing the binder to form an implant green part; and c$_1$. infiltrating the implant green part; or c$_2$. sintering the implant green part to form an implant, wherein the calcium phosphate composition does not decompose to produce water during step b, and the implant has a designed complex three-dimensional shape with a well-defined cavity, the cavity having an opening to a surface, the opening having a smaller cross sectional area than the cavity, has a controlled, interconnected porosity, and has a mole ratio of calcium to phosphorus of 0.5 to 1.

20. An implant produced by selectively fusing a calcium phosphate composition with a binder to form an implant green part; and sintering the implant green part to form an implant, wherein the calcium phosphate composition does not decompose to produce water during fusing, and the implant has a designed complex three-dimensional shape with a well-defined cavity, the cavity having an opening to a surface, the opening having a smaller cross sectional area than the cavity, has a controlled, interconnected porosity, and has a mole ratio of calcium to phosphorus of 0.5 to 1.

21. An implant produced by selectively fusing a calcium phosphate composition with a binder to form an implant green part; infiltrating the green part, and sintering the green part to form an implant, wherein the calcium phosphate composition does not decompose to produce water during fusing, and the implant has a designed complex three-dimensional shape with a well-defined cavity, the cavity having an opening to a surface, the opening having a smaller cross sectional area than the cavity, has a controlled, interconnected porosity, and has a mole ratio of calcium to phosphorus of 0.5 to 1.

22. An implant produced by a. forming a mixture of particles of a calcium phosphate composition and a binder;

b. forming a layer of the mixture;

c. selectively fusing the binder;

d. repeating steps b. and c. a desired number of times to form a plurality of layers, wherein each layer is fused to adjacent layers to form the implant green part; and e$_1$. infiltrating the implant green part; or e$_2$. sintering the implant green part to form an implant, wherein the calcium phosphate composition does not decompose to produce water during step c, and the implant has a designed complex three-dimensional shape with a well-defined cavity, the cavity having an opening to a surface, the opening having a smaller cross sectional area than the cavity, has a controlled, interconnected porosity, and has a mole ratio of calcium to phosphorus of 0.5 to 1.

* * * * *

UNITED STATES PATENT AND TRADEMARK OFFICE
CERTIFICATE OF CORRECTION

PATENT NO. : 6,183,515 B1
DATED : February 6, 2001
INVENTOR(S) : Barlow et al.

It is certified that error appears in the above-identified patent and that said Letters Patent is hereby corrected as shown below:

<u>Column 25, claim 8,</u>
Line 11, delete the word "or" immediately preceding 'wherein'.

Signed and Sealed this

Twenty-third Day of October, 2001

Attest:

NICHOLAS P. GODICI
*Attesting Officer*   *Acting Director of the United States Patent and Trademark Office*